(12) United States Patent
Tesfazion et al.

(10) Patent No.: US 11,241,410 B2
(45) Date of Patent: Feb. 8, 2022

(54) METHOD AND COMPOUND FOR THE TREATMENT OF COVID-19

(71) Applicants: Amanuel Tesfazion, Washington, DC (US); Lydia Seifu, Silver Spring, MD (US); Meried Bezuneh, Alexandria, VA (US)

(72) Inventors: Amanuel Tesfazion, Washington, DC (US); Lydia Seifu, Silver Spring, MD (US); Meried Bezuneh, Alexandria, VA (US)

( * ) Notice: Subject to any disclaimer, the term of this patent is extended or adjusted under 35 U.S.C. 154(b) by 0 days.

(21) Appl. No.: 16/945,600

(22) Filed: Jul. 31, 2020

(65) Prior Publication Data

US 2021/0353582 A1   Nov. 18, 2021

Related U.S. Application Data

(60) Provisional application No. 63/026,575, filed on May 18, 2020.

(51) Int. Cl.
*A61K 31/235*   (2006.01)

(52) U.S. Cl.
CPC .................................. *A61K 31/235* (2013.01)

(58) Field of Classification Search
CPC ... A61K 36/00; A61K 2300/00; A61K 31/235
See application file for complete search history.

(56) References Cited

U.S. PATENT DOCUMENTS 7,144,922 B2 * 12/2006 Demssie .............. A61K 31/235
514/772.3

OTHER PUBLICATIONS

Miller (https://www.businessinsider.com/exercise-may-help-prevent-a-deadly-coronavirus-complication-2020-4), 2020 (Year: 2020).*
Webmd, 2021 (Year: 2021).*
Wikipedia, 2021 (Year: 2021).*
Gollakner, https://vcahospitals.com/know-your-pet/ coronavirus-disease-in-dogs (Year: 2021).*
School of Medicine and Public Health, University of Wisconsin, 2017). (Year: 2017).*
Benzie, Herbal Medicine: Biomolecularand Clinical Aspects, 2nd Ed. 2011 (Year: 2011).*
Dance, 2021, https://www.scientific american.com/article/why-its-so-hard-to-make-antiviral-drugs-for-covid-and-other-diseases/ (Year: 2021).*

* cited by examiner

*Primary Examiner* — Umamaheswari Ramachandran
(74) *Attorney, Agent, or Firm* — The Iwashko Law Firm, PLLC; Lev Ivan Gabriel Iwashko

(57) ABSTRACT

A method for the treatment of a coronavirus disease, including administering to a subject in need thereof of an anti-pathogenic compound, such that the anti-pathogenic compound is derived from an herbal extract.

13 Claims, 15 Drawing Sheets

Molecular Structure of Dietylene glycol dibenzoate

II – 1,3–disubstituted–phenyl–2–propen–1–one

Diethylene glycol dibenzoate

METHOD AND COMPOUND FOR THE TREATMENT OF COVID-19

CROSS REFERENCE TO RELATED APPLICATION

This application claims the benefit of, and incorporates by reference, U.S. provisional patent application Ser. No. 63/026,575, entitled "Method and Compound for the Treatment of COVID-19," which was filed on May 18, 2020.

BACKGROUND

1. Field

The present general inventive concept relates generally to treatment of a viral disease, and particularly, to a method and compound for the treatment of coronavirus disease 2019 (COVID-19).

2. Description of the Related Art

In December 2019, a novel form of pneumonia caused by an unknown pathogen was discovered in Wuhan, China. Subsequently, the unknown pathogen has been identified as severe acute respiratory syndrome coronavirus 2 (SARS-CoV-2).

As with other coronaviruses, SARS-CoV-2 has a zoonotic (i.e. animal) origin. Coronaviruses are often carried by bats, though other animals may be a carrier of this particular group of viruses. Currently, a pangolin is believed to be the intermediate host between bats and humans, but the precise vector of animal-to-human transmission remains unknown.

The World Health Organization (WHO) has named the disease caused by SARS-CoV-2 as COVID-19. Since December 2019, COVID-19 has spread rapidly worldwide. On Mar. 11, 2020, the WHO declared COVID-19 a pandemic due to local human-to-human transmission of the disease within each region monitored by the WHO.

At the beginning of May 2020, reported worldwide cases of COVID-19 exceeded 3.4 million and the death toll was over 240,000. At the same time, in the United States alone, the number of cases surpassed 1.1 million and the number of deaths was over 57,000.

Unfortunately, symptoms among people infected with COVID-19 widely vary, which makes prevention difficult. Some of the more common symptoms include fever and cough, whereas other people may show no symptoms at all. Also, unlike other common diseases, the incubation period of COVID-19 ranges from two to fourteen days, which increases the difficulty of prevention. For at least these reasons, the importance of treating people infected with COVID-19 is apparent.

Due to the novelty of SARS-CoV-2, humans have no natural immunity. The lack of immunity facilitates human-to-human transmission of COVID-19. Moreover, the pandemic has and/or may continue to overwhelm healthcare systems depending on precautions taken within the community worldwide. More specifically, until a vaccine is developed, alternative methods of prevention include social distancing, quarantining, and/or use of personal protective equipment, such as a face mask.

The WHO has not identified any specific treatment for COVID-19. As such, most researchers have begun testing the effects of existing medication.

In vitro clinical trials of two antimalarial drugs, chloroquine and hydroxychloroquine, have been performed. Both drugs have demonstrated some activity against SARS-CoV-2 in infected Vero E6 cells. There is some evidence it may block infection in Vero E6 cells exposed to SARS-CoV-2. Prior in vitro testing has shown active prevention against severe acute respiratory syndrome coronavirus (SARS-CoV-1) and middle east respiratory syndrome coronavirus (MERS-CoV). Unfortunately, both drugs have a known pharmacokinetics and toxicity profile.

Hydroxychloroquine has similar mechanisms of action as chloroquine and adverse effects may have a more favorable dose related toxicity profile than chloroquine, but cardiotoxicity is a concern with both drugs. At present, there is only limited clinical trial data available to evaluate use of chloroquine for treatment and/or prevention of COVID-19. Multiple clinical trials have been initiated using various dosages in patients with COVID-19 in China and other countries globally. Clinical reports of possible benefits, including a decrease in viral load and duration of illness is based on limited data available to support efficacy and identify possible safety concerns in patients with COVID-19.

The in vitro study of hydroxychloroquine showed that it could prevent SARS-CoV-2 from entering cells in a petri dish, by way of changing the pH of endosomes believed to prevent viral entry, transport, and post-entry events. While it shows a plausible mechanism for the drug, the effects on cells in the petri dish can vary when evaluating cells in living people.

Clinical trials of hydroxychloroquine, by contrast, have so far yielded mixed results. Each of the studies performed across the globe, including France and China, included a very small sample set of eleven to thirty-six patients. As such, the trial wasn't randomized, which potentially skews the results. The study in France found that hydroxychloroquine was ineffective at best, with one out of eleven patients dying, two were transferred to an intensive care unit, and one patient who experienced a dangerous heart problem and had the hydroxychloroquine treatment terminated early. In Sweden, some hospitals stopped offering the drug after some patients reported seizures and blurred vision.

The listed side effects of hydroxychloroquine are long and well-known. The Food and Drug Administration (FDA) has reported problems like irreversible retinal damage, cardiac arrhythmias, muscle weakness, and a severe drop in blood sugar. There are psychiatric effects as well, including insomnia, nightmares, hallucinations, and suicidal ideation. The drug can also have harmful interactions with medicines used to treat diabetes, epilepsy, and heart problems.

It is also believed that chloroquine may have a varied mechanism of action which may differ depending upon the pathogen studied. It has been increasingly learnt that the antiviral and anti-inflammatory activities of chloroquine may have a role in the treatment of patients with COVID-19. Chloroquine increases endosomal pH and interferes with the glycosylation of cellular receptor of SARS-CoV and thereby it has the potential to block viral infection.

In addition, chloroquine also inhibits the quinone reductase-2, which is involved in sialic acid biosynthesis (an acidic monosaccharides of cell transmembrane proteins required for ligand recognition) that makes this agent a broad antiviral agent. It is important to note that both human coronavirus HCoV-O43 and orthomyxoviruses uses sialic acid moieties as a receptor.

Chloroquine changes the pH of lysosomes and likely inhibits cathepsins that leads to the formation of the autophagosome which cleaves the SARS-CoV-2 spike protein. In other words, chloroquine breaks down peptide bonds between amino acids in proteins.

Furthermore, chloroquine, through the inhibition of MAP-kinase, interferes with SARS-CoV-2 molecular crosstalk, besides altering the virion assembly, budding and interfering with the proteolytic processing of the M protein. In vitro studies indicate that the antiviral effect of chloroquine diphosphate requires a high concentration of the drug. (See Effect of High vs Low Doses of Chloroquine Diphosphate as Adjunctive Therapy for Patients Hospitalized With Severe Acute Respiratory Syndrome Coronavirus 2 (SARS-CoV-2) Infection, Mayla Gabriela Silva Borba, MD; Fernando Fonseca Almeida Val, PhD; Vanderson Souza Sampaio, PhD; et al, JAMA).

Experimental studies have suggested that chloroquine is a proven antimalarial drug that has the capability of inhibiting the replication of several intracellular microorganisms including coronaviruses in vitro.

The empirical evidence for the clinical effectiveness of chloroquine in COVID-19 is currently very limited. First, clinical results were reported in a news briefing by the Chinese government in February 2020, revealing that the treatment of over one hundred patients with chloroquine phosphate in China had resulted in significant improvements of pneumonia and lung imaging, with reductions in the duration of the illness. No adverse events were reported.

A group of Brazilian researchers planned to enroll four hundred forty people in a double-blind study. However, after enrolling just eighty-one patients, researchers saw concerning signs. Within just a few days of starting treatment, more patients in the high dose group experienced heart rhythm problems than did those in the low dose group. Moreover, two patients in the high dose group developed a fast, abnormal heart rate known as ventricular tachycardia before they died. The high dose arm of the study (600 mg administered twice daily for 10-days) was immediately halted. Researchers wrote in their paper, posted Apr. 11, 2020 to the pre-print database medRxiv, "Our study raises enough red flags to stop the use of such [high] dosage . . . worldwide in order to avoid more unnecessary deaths". (See "Trial of chloroquine to treat COVID-19 stopped early due to heart complications", LiveScience, By Rachael Rettner). The preliminary findings of this study suggest that the higher chloroquine dosage should not be recommended for critically ill patients with COVID-19 because of its potential safety hazards, especially when taken concurrently with azithromycin and oseltamivir. These findings cannot be extrapolated to patients with non-severe COVID-19 (See JAMA above).

Chloroquine has been in clinical use for several years. Thus, its safety profile is well established. The Centre for Evidence-Based Medicine (CEBM), which develops, promotes, and disseminates better evidence of health care reported isolated cases of cardiomyopathy and heart rhythm disturbances caused by treatment with chloroquine. Chloroquine should be avoided in patients with porphyria (i.e. a group of disorders that result from a buildup of natural chemicals that produce porphyrin in your body). Both chloroquine and hydroxychloroquine are metabolized in the liver with renal excretion of some metabolites, hence they should be prescribed with care in people with liver or renal failure.

Clinical, randomized, open-label trials of Lopinavir (LPV) and Ritonavir (RTV) have been performed on randomized hospitalized adults with severe COVID-19 symptoms. LPV/RTV are human immunodeficiency virus (HIV and/or HIV-1) protease inhibitor drugs that shown in vitro activity against SARS-CoV and MERS-CoV. There appeared to be some evidence that LPV/RTV initiation within twelve days after symptom onset is associated with shorter time to clinical improvement. However, there is otherwise no significant differences in reduction of viral ribonucleic acid (RNA) load, duration of viral RNA detectability, duration of oxygen therapy, duration of hospitalization, or time from randomization to death. In this case, the LPV/RTV trial stopped early because of adverse effects.

LPV is widely used for the treatment of HIV and is a potential candidate for the treatment of COVID-19. LPV is formulated in combination with another protease inhibitor, RTV. RTV inhibits the metabolizing enzyme cytochrome P450 3A and therefore increases the half-life of LPV. The SARS-CoV-2 virus is a single-stranded RNA beta-coronavirus, similar to SARS-CoV and MERS-CoV. These viruses enter host cells and replicate, producing strands that contain multiple copies of the viral genetic material RNA. The strands of genetic material accumulate at the periphery of the cell, ready to be cleaved, packaged, and prepared for release from the host cell. The enzyme 3-chymotrypsin-like protease (3CLP') plays a crucial role in processing the viral RNA. As LPV is a protease inhibitor, it may inhibit the action of $3CL^{pro}$, thereby disrupting the process of viral replication and release from host cells (See https://www.cebm.net/covid-19/lopinavir-ritonavir-a-rapid-review-of-the-evidence-for-effectiveness-in-treating-covid/).

Currently, there is no strong evidence for the efficacy of LPV/RTV in the treatment of COVID-19. Overall, the limited studies identified were subject to methodological flaws. Several ongoing trials of LPV/RTV are still recruiting.

The latest trial evidence suggests that LPV has antiviral activity against SARS-CoV-2 in vitro. However, coronavirus proteases, including $3CL^{pro}$, do not contain a C2-symmetric (i.e. bidentate ligands (an ion or molecule that binds to a central metal atom to form a coordination complex) that are dissymmetric, but not asymmetric by virtue of their C2-symmetry) pocket, which is the target of HIV protease inhibitors, leading some to question the potential potency of HIV protease inhibitors in treating these viruses.

There is some preliminary evidence of the effectiveness of LPV/RTV against other coronaviruses. In vivo, an open-label, non-randomized study found a reduced risk of severe hypoxia or death in forty-one SARS-CoV patients who were treated with LPV/RTV and ribavirin, compared to one hundred eleven historical controls treated with ribavirin alone. There has been no evidence from randomized trials of the efficacy of LPV/RTV in treating SARS-CoV or MERS-CoV.

In terms of safety, side effect profile and drug interactions of LPV/RTV is contraindicated in porphyria and caution is advised in patients with haemophilia, cardiac conduction disorders, pancreatitis, patients at increased risk of cardiovascular disease and those with structural heart disease. Common side effects include gastrointestinal disturbance, in particular diarrhea, which is often worse in the first few weeks. Dyslipidaemia, diabetes mellitus, pancreatitis, and hepatic disorders have also been reported. Drug interactions with LPV are common due to their inhibition of cytochrome P450, which can lead to increased levels of co-administered drugs that are metabolized by this enzyme. Drugs that interact with LPV and are commonly used in primary care include simvastatin, combined oral contraceptives, anti-epileptic drugs, and inhaled fluticasone.

Remdesivir is a broad antiviral drug used to treat different diseases and has previously been tested on SARS-CoV, MERS-CoV, and Ebola. It has demonstrated in vitro activity against SARS-CoV-2. Clinical phase 3, randomized, open-label trials of Remdesivir have been initiated by a manufacturer, Gilead, to evaluate safety and antiviral activity of Remdesivir in patients with severe COVID-19. Also, Gilead has begun phase 3, randomized, open-label trials of Remdesivir to evaluate safety and antiviral activity of Remdesivir in patients with moderate COVID-19. Lastly, Gilead has begun phase 2, randomized, placebo-controlled trials sponsored by NIAID initiated to evaluate safety and efficacy of Remdesivir in hospitalized patients with laboratory-confirmed COVID-19.

While in vitro results suggest the drug works by blocking the RNA in SARS-CoV-2 from replicating, laboratory findings do not always translate to findings in people. The clinical assessment of Remdesivir prematurely stopped early due to too few patients. Patients in the Remdesivir trial ranged in age from twenty-three to eighty-two years old. Thirty-six patients needed less oxygen support over a median follow-up of eighteen days. Seven patients died. More than half of those on ventilation were taken off ventilation. Also, nearly half of those hospitalized were discharged (See https://www.webmd.com/lung/news/20200414/remdesivir-for-covid-study-benefits-not-clear).

It is important again to note that the drug was not tested against a placebo, so there is no way to know if the patients improved on their own. Additionally, the follow-up was brief, and only forty patients got the full-length treatment. According to a summary of a study in China, Remdesivir was "not associated with a difference in time to clinical improvement" compared to a standard of care control. After one month, it appeared 13.9% of the Remdesivir patients had died compared to 12.8% of patients in the control arm. The difference was not statistically significant.

"In this study of hospitalized adult patients with severe COVID-19 that was terminated prematurely, Remdesivir was not associated with clinical or virological benefits," the summary states (See https://www.statnews.com/2020/04/23/data-on-gileads-remdesivir-released-by-accident-show-no-benefit-for-coronavirus-patients/).

Therefore, due to the COVID-19 pandemic, there is an immediate need for an effective remedy that is natural, inexpensive, and non-toxic. As such, there is a need for a method and compound for the effective treatment of COVID-19.

SUMMARY

The present general inventive concept provides a method and compound for the treatment of COVID-19.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a method for the treatment of a coronavirus disease, including administering to a subject in need thereof of an anti-pathogenic compound, such that the anti-pathogenic compound is derived from an herbal extract.

The herbal extract may be a glycol derivative.

The glycol derivative may be diethylene glycol dibenzoate.

The coronavirus disease may be COVID-19.

The foregoing and/or other features and utilities of the present general inventive concept may also be achieved by providing a method of strengthening a subject infected with a coronavirus disease, including administering to the subject in need thereof of an anti-pathogenic compound, such that the anti-pathogenic compound is derived from an herbal extract.

The herbal extract may be a glycol derivative.

The coronavirus disease may be COVID-19.

The anti-pathogenic compound may boost an immune system of the subject.

Boosting the immune system may include revitalizing at least one of a dysfunctional monocyte and a dysfunctional macrophage.

Boosting the immune system may include stimulating production of gamma interferon.

Boosting the immune system may use only the anti-pathogenic compound.

BRIEF DESCRIPTION OF THE DRAWINGS

These and/or other features and utilities of the present generally inventive concept will become apparent and more readily appreciated from the following description of the embodiments, taken in conjunction with the accompanying drawings of which.

DETAILED DESCRIPTION

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

Figure 1A:
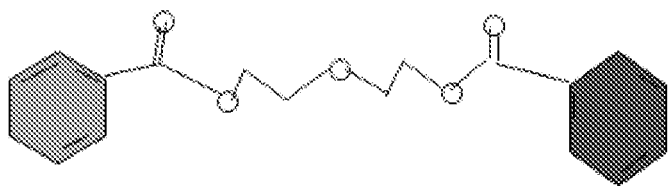
FIG. 1A illustrates a molecular structure of an anti-pathogenic compound, known as 90I (diethylene glycol dibenzoate), according to an exemplary embodiment of the present general inventive concept.

FIG. 1A illustrates a molecular structure of an anti-pathogenic compound, known as 90I (diethylene glycol dibenzoate), according to an exemplary embodiment of the present general inventive concept.

Figure 1B:
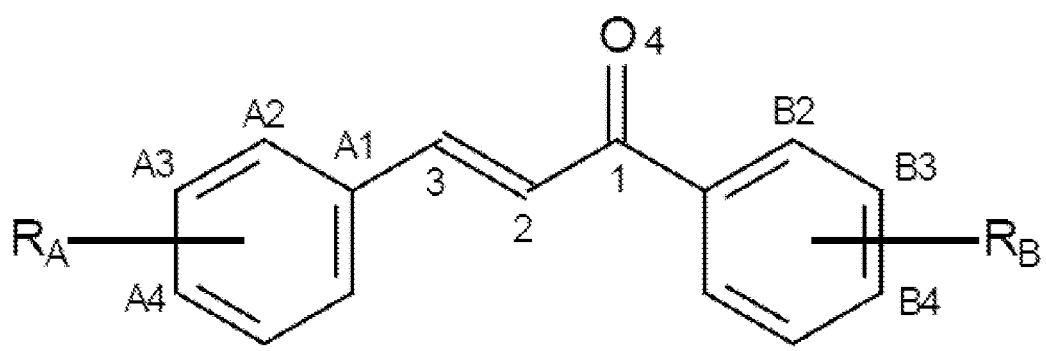
FIG. 1B illustrates a molecular structure of the anti-pathogenic compound, known as 90I, according to an exemplary embodiment of the present general inventive concept.
Figure 2:
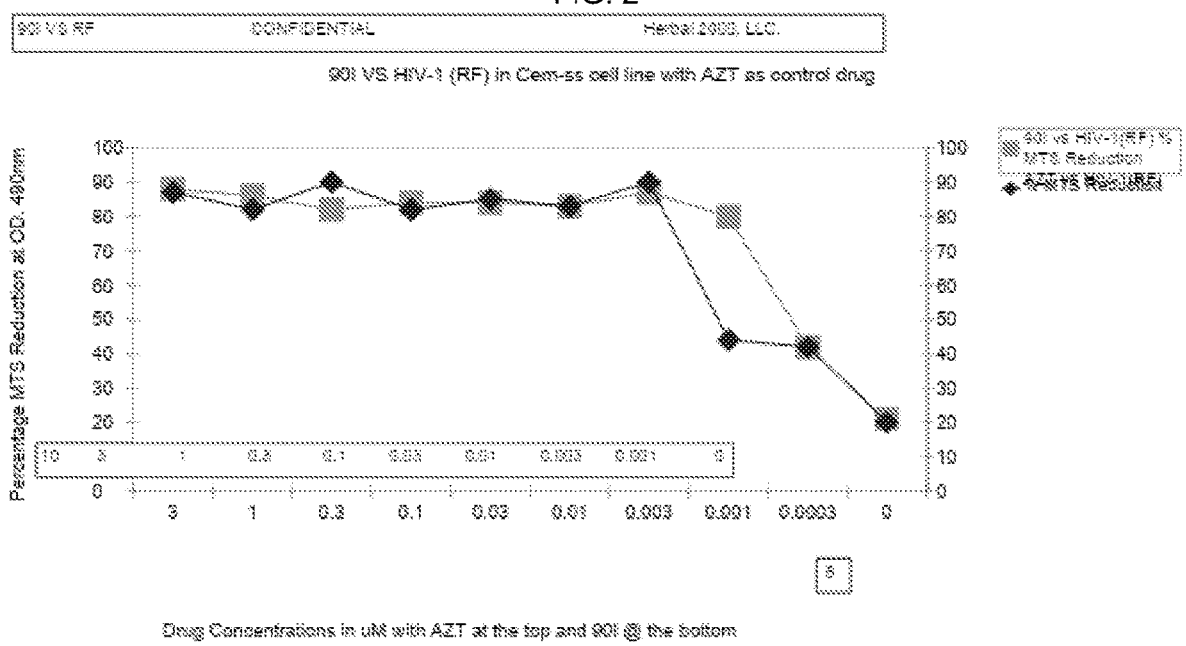
FIG. 2 illustrates a graph showing an effect of 90I compared to AZT on HIV in CEM-SS cells, according to an exemplary embodiment of the present general inventive concept.

FIG. 1B illustrates a molecular structure of the anti-pathogenic compound, known as 90I, according to an exemplary embodiment of the present general inventive concept.

A novel molecule has been discovered within an herb located in Ethiopia that may be used to treat subjects (e.g., people, animals, etc.) infected with a pathogen, which in this case is COVID-19. However, although treatment is the term used, treatment may also include prophylaxis (i.e. prevention) and/or vaccination, such that the treatment may inhibit replication of and/or kill the pathogen. The observed window of efficacy at a traditional herbal treatment center in Ethiopia, used in treating AIDS patients, served as the basis for undertaking the developmental investigation of the crude product for further drug development investigation.

Furthermore, although the pathogen is identified as COVID-19, 90I may be used to treat any pathogen including a virus, bacteria, protozoan (i.e. parasite), and/or fungal. As such, any infection, disease, or illness may be treatable by 90I.

Bacterial pathogens may include *Mycobacterium tuberculosis* Tuberculosis, *Bacillus anthracis* Anthrax, and *Staphylococcus* Sepsis *aureus*, but are not limited thereto.

Viral pathogens may include Adenoviridae, Mastadenovirus, Infectious canine hepatitis, Arenaviridae, Arenavirus, Lymphocytic choriomeningitis, Caliciviridae, Norovirus, Norwalk virus infection, Coronaviridae, Coronavirus, Severe Acute Respiratory Syndrome, SARS-CoV, SARS-CoV-2, Torovirus, Filoviridae, Marburgvirus, Viral hemorrhagic fevers, Ebolavirus, Viral hemorrhagic fevers, Flaviviridae, Flavivirus, West Nile Encephalitis, Hepacivirus, Hepatitis C virus infection, Pestivirus, Bovine Virus Diarrhea, Classical swine fever, Hepadnaviridae, Orthohepadnavirus, Hepatitis, Herpesviridae, Simplexvirus, cold sores, genital herpes, bovine mammillitis, Varicellovirus, chickenpox, shingles, abortion in horses, encephalitis in cattle, Cytomegalovirus, infectious mononucleosis, Mardivirus, Marek's disease, Orthomyxoviridae, Influenzavirus A, Influenza, Influenzavirus B, Influenza, Papillomaviridae, Papillomavirus, Skin warts, skin cancer, cervical cancer, Picornaviridae, Enterovirus, Polio, Rhinovirus, Common cold; Aphthovirus, Foot-and-mouth disease, Hepatovirus, Hepatitis, Poxviridae, Orthopoxvirus, Cowpox, vaccinia, smallpox, Reoviridae, Rotaviruses, Diarrhea, Orbivirus, Blue tongue disease, Retroviridae Gammaretrovirus, Feline leukemia, Deltaretrovirus, Bovine leukemia, Lentivirus, Human immunodeficiency, FIV, and SIV, Rhabdoviridae, Lyssavirus, Rabies, Ephemerovirus, Bovine ephemeral fever, Togaviridae, Alphavirus, and Eastern and Western equine encephalitis, but are not limited thereto.

Parasitic pathogens may include *Plasmodium, Malaria, Leishmania,* and Leishmaniasis, but are not limited thereto.

Fungal pathogens may include Aspergillis, *Candida*, Coccidia, Cryptococci, *geotricha, Histoplasma*, Microsporidia, and *Pneumocystis*, but is not limited thereto.

As such, 90I may also be an anti-pathogenic compound that is applicable to different diseases and/or infections.

The Ethiopian region may be characterized by a wide range of ecological, edaphic, and climatic conditions that account for the wide diversity of its biological resources, both in terms of flora and faunal wealth. The plant genetic resources of the country exhibit an enormous diversity as seen in the fact that Ethiopia is one of the twelve Vavilov Centers of origin for domesticated crops and their wild and weedy relatives. According to recent studies, it is estimated that there are more than seven thousand species of flowering plants recorded in Ethiopia, of which at least twelve percent are probably endemic.

Medicinal plants may comprise one of the important components of Ethiopian vegetation. On record, there may be six hundred species of medicinal plants constituting a little over ten percent of Ethiopia's vascular flora. The medicinal plants may be distributed all over the country, with greater concentration in the south and southwestern parts of the country. Woodlands of Ethiopia may be the source of most of the medicinal plants, followed by the montane grassland and/or dry montane forest complex of the plateau. Other important vegetation types for medicinal plants may be the evergreen bushland and rocky areas.

As such, an herbal extract may be extracted from the herb from Ethiopia. The herbal extract may include a glycol derivative. Moreover, the glycol derivative may include diethylene glycol dibenzoate. An anti-pathogenic compound may include diethylene glycol dibenzoate to treat HIV-1.

HIV-1 may have the best complicated strategy for survival than any microbial known to man. HIV-1 may replicate more than one billion virion every day in every patient, but its replication process is error prone when the reverse transcriptase (RT) (i.e. an enzyme that catalyzes the formation of DNA from an RNA template in reverse transcription) transcribes the viral RNA to DNA.

HIV-1 in vitro data analysis of 90I, via Bioassay Guided Fractionation, may confirm observed in vivo data and was used to isolate a lead molecule.

Full blown in vitro studies may demonstrate astonishing results that surpass any known commercially available antiretroviral (ARV) and/or highly active antiretroviral therapy (HAART) drugs currently on the market.

Referring to FIGS. 1A and 1B, an anti-pathogenic agent and/or the anti-pathogenic compound may be identified as 90I (or 90i). The anti-pathogenic compound may be derived from the herbal extract identified as H2K1001. H2K1001 and/or 90I may be a natural product that was isolated using the Bioassay Guided Fractionation, and further purified, molecularly characterized (i.e. characterizing at the molecular level without any effect of environment or development or physiological state of the organism), and not only found to be highly potent against all HIV-1 strains, but also immunogenic with unique multiple modes of action (i.e. functional or anatomical change at a cellular level, resulting from exposure of a living organism to a substance), potently effective against both reverse transcriptase and a protease (PR) enzyme (i.e. an enzyme which breaks down proteins and peptides). The essence of combination drug therapy, HAART regiments, may be its effectiveness against all HIV-1 strains that is potent enough to bring the viral load down to undetectable level. This may be achieved by combining an RTI and a PRI combination synergy to affect multiple mode of action.

However, this approach by other drugs may favor the HIV virus' natural selection to evade drug therapy by mutating at a single amino acid sequence and/or a plurality of amino acid sequences.

In contrast, 90I may operate alone with multiple modes of action working against both RT and a PR that is effective against all HIV-1 and highly potent may bring the viral load to undetectable level with added advantages of easy to take, no toxicity, and an effective immune booster as well as its synergic advantages at a low drug concentration level. For example, an immune booster may include an immunostimulant, such as drugs and/or nutrients that stimulate an immune response by inducing activation and/or increasing activity of any of its components.

Furthermore, 90I may have a low molecular weight and/or lead structures that have a natural configuration and topology. Additionally, 90I may be thermodynamic, hydrophobic, electric, and/or stereo-geometric, such that 90I may be active against a wide range of molecular targets.

As such, 90I may be considered a miracle molecule, and may also be known as a miracure, miracule, and/or molecure, but is not limited thereto.

Antiviral Drug Assay in CEM-SS Cells

FIG. 2 illustrates a graph showing an effect of 90I compared to AZT on HIV in CEM-SS cells, according to an exemplary embodiment of the present general inventive concept.

Referring to FIG. 2, an initial evaluation of 90I and/or H2K1001 in the CEM-SS (i.e. human T-cells that are permissive to HIV-1 infection) cell line demonstrated significant antiviral activity against the RF laboratory strain of HIV-1. The purified fraction 90I may yield a 50% effective concentration (EC50) of 0.020 ug/ml. At the same time, there was no discernible drug induced toxicity in this study (50% inhibitory concentration (IC50) was greater than the high-test concentration of 100 ug/ml). The resulting therapeutic index (TI=IC50/EC50) of greater than 5000 suggests a highly active compound. An azidothymidine (AZT) control in this study was included to ensure the functionality of all antiviral testing, which yielded an EC50 of approximately 0.0035 uM, an 1050 greater than 10 uM and a TI of greater than 2857.

Figure 3:
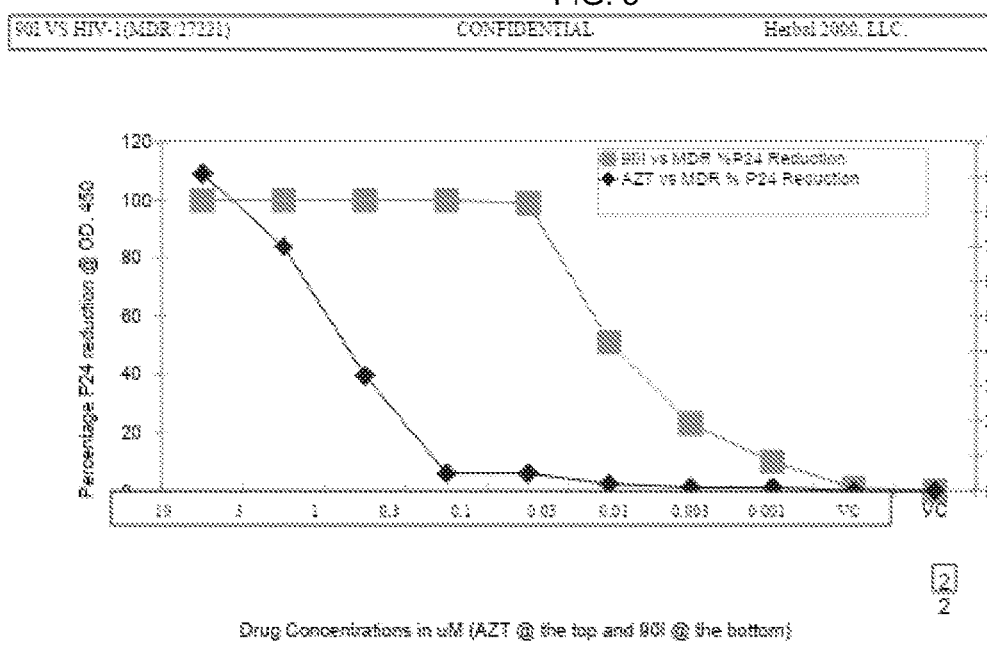
FIG. 3 illustrates a graph showing inhibitory activity of 90I compared to AZT on an MDR-27221 HIV strain, according to an exemplary embodiment of the present general inventive concept.

FIG. 3 illustrates a graph showing inhibitory activity of 90I compared to AZT on an MDR-27221 HIV strain, according to an exemplary embodiment of the present general inventive concept.

Referring to FIG. 3, additionally, evaluation of 90I against a multi-drug resistant (MDR) HIV-1 strain (e.g., MDR-27221), a clinical isolate resistant to nucleoside reverse transcriptase inhibitors (NRTIs), non-nucleoside reverse transcriptase inhibitors (NNRTIs), and protease inhibitors (PRIs), showed a strong inhibitory activity at EC50 of 3 ug/ml and a TI of >333. The control drug, AZT, with EC50 of 3 uM failed, as expected, to inhibit the MDR strain. This finding may be significant because most of the failure of antiretroviral therapy stems from an emergence of a drug resistant virus.

Furthermore, a resistance conferring mutation has been identified for virtually all antiretroviral agents in clinical practice. A test virus parental stock originated from a genotypic antiretroviral resistance test (GART) study. Additionally, a clinical isolate was pre-confirmed for genetic and phenotypic variance prior to this test. In the previous study, 90I and/or H2K1001 may have demonstrated its effectiveness against an NRTI and/or NNRTI resistant virus, and in this study, it has significantly shown high activity against all NRTI, NNRTI, and PRI resistant varieties. Accordingly, the fact that 90I may be effective against MDR viruses with multiple modes of action, it can replace the need for combination HIV drug therapy. This finding may be highly significant because typical current single target-oriented designer antiretroviral drugs have seriously been challenged by resistant viruses. Due to natural selection, the HIV-1 virus may have developed several survival strategies that include mutation.

Figure 4:
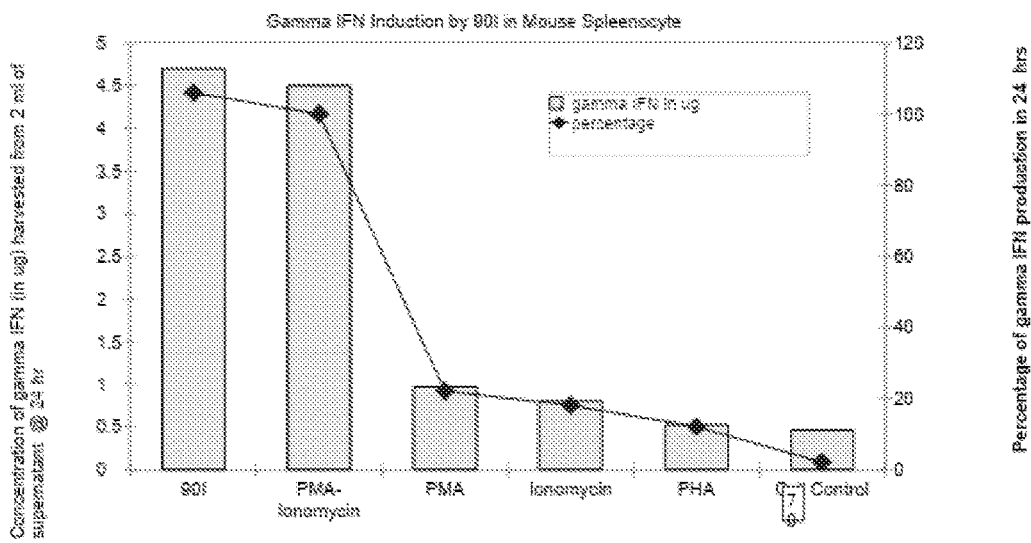
FIG. 4 illustrates a graph showing production of gamma interferon by cells receiving 90I compared to other drugs, according to an exemplary embodiment of the present general inventive concept.

FIG. 4 illustrates a graph showing production of gamma interferon by cells receiving 90I compared to other drugs, according to an exemplary embodiment of the present general inventive concept.

Referring to FIG. 4, furthermore, 90I has proven to stimulate the production of gamma interferon (i.e. a dimerized soluble cytokine that is the only member of the type II class of interferons and is a product of human leukocytes and human lymphocytes). More specifically, 90I may migrate from blood into tissue and differentiate into tissue macrophages, such that each of the tissue macrophages may serve as a vehicle for transporting viruses to a variety of tissues. The ability of antiretroviral agents to cross the blood brain barrier is one important consideration, since the brain acts as a sanctuary for viruses as well as a site for disease progression.

This assay may underscore 90I's absorptions in a monocyte and/or a macrophage primary cell, such that the anti-pathogenic compound may have stability and longer pharmacokinetic half-life in ten days assay with single time point drug addition. Another significance of this result is that 90I and/or HK1001 may reinstate a dysfunctional monocyte to resume its natural functional role as a primary effector cell in the cellular immune system, effecting extensive anti-microbial and/or anti-fungal functional capability in the killing of multiple pathogens and/or other opportunistic infecting agents, such as COVID-19.

Referring again to FIG. 4, activated CD8+ cells are reported to produce high levels of gamma interferon, which may be involved in the anti-HIV-1 immune responses, contributing to both control of viral spread and concomitant lymphoid follicular lyses. An amount of gamma interferon produced by 90I may be equivalent to that of the positive control, PMA-Ionomycin combination. The conclusion from this result may be that 90I stimulates cellular genes to produce gamma interferon. This finding may have a far-reaching implication and relevant to interleukin 12 (IL-12) (i.e. a cytokine that is produced by activated antigen-presenting cells, such as dendritic cells and/or macrophages). The Th-2 subset may favor a humeral response, including IL-4, IL-5, and IL-6 and causes activation of B cells (i.e. B lymphocytes) leading to antibody formations.

Therefore, the above findings require further evaluation of the efficacy of 90I with other infectious agents, in particular tuberculosis, Hepatitis C, Malaria, and most recently COVID-19 through the use of molecular docking (i.e. a kind of bioinformatic modeling which involves the interaction of two or more molecules to give the stable adduct).

In contrast to the other current therapies being used, 90I may be a non-toxic product, due to its source coming from a natural product. This is evident in the HIV in vitro tests results, as seen below in Table 1. As described above, it is critical to point out that each of the clinical trials, which have been discontinued, has been due to observed toxicity that has led to patient deaths in several cases. While the FDA has issued a "compassion use" policy for any therapies that may be currently in use due to the nature of the COVID-19 pandemic, 90I may already be compliant due to its development from a natural product for the use of COVID-19 therapeutics.

TABLE 1

| Drugs | EC50(uM) | TI |
|---|---|---|
| AZT | 0.001 | >1000 |
| ddc | 0.001 | >200 |
| ddI | 0.0056 | >1760 |
| 90I | 0.0003 | >5000 |
| Indinivir | 0.005 | >1000 |
| Neverepin | 0.048 | >1000 |
| Retinovir | 0.002 | >1000 |
| Saquinovir | 0.0012 | >2000 |

To put a new drug on the market may take over ten years to develop with costs of upwards of three million dollars. In order to minimize the time and money invested in investigating molecules, virtual screening may become more frequently used by organizations, researchers, etc.

Structural analyses of a viral and/or a bacterial molecule in combination with a molecule of perspective drug provides an essential framework for understanding of the molecular mechanisms of protein processing, RNA and/or DNA replication, and viral and/or bacterial assembly which contribute to a better understanding of the pathogenesis of disease-causing viruses and/or bacteria alike.

Unlike any of the existing therapies for COVID-19 to date (i.e. the repurposing of anti-HIV protease inhibitors, anti-malaria, antiviral agents, and interferon stimulants), 90I may reinstate dysfunctional monocytes, may use proven multiple modes of action against protease and reverse transcriptase, and any may exhibit promising auto dock virtual experiments, such that 90I may be an ideal candidate for further evaluation in treatment of COVID-19.

Implementation of a proposed plan will consist of performing an in vitro study to evaluate 90I with SARS-CoV-2, as described in greater detail below, and an in vivo study, once approved. Given the state of the ongoing SARS-CoV-2 epidemic, the FDA has released a "Guidance on Conduct of Clinical Trials of Medical Products during the COVID-19 Public Health Emergency." The FDA plays a critical role in protecting the United States from threats including emerging infectious diseases, including the Coronavirus Disease 2019 (COVID-19) pandemic. The FDA is committed to providing timely guidance and general considerations to assist sponsors in assuring the safety of trial participants, maintaining compliance with good clinical practice (GCP), and minimizing risks to trial integrity during the COVID-19 public health emergency. All regulatory standards may be followed to ensure good clinical practice and minimizing any risks during testing.

Additionally, in vivo protocol may follow the gold standard. The gold standard for figuring out cause and effect may include a double-blind randomized controlled trial. Patients may be sorted randomly between those receiving the treatment, those in the control group, and/or those receiving a placebo. To make a study double-blind, not only do the patients not know if they are receiving the active treatment, but also the people administering it don't know, thus controlling for unintentional bias. When large enough with sufficient numbers of people, these trials may yield robust results and overcome biases that emerge in smaller samples, such as having a certain age demographic overrepresented in the study group.

Incidentally, it is critical to point out the clinical trials described above for hydroxychloroquine, chloroquine, Remdesiver, and LPV/RTV failed to adhere to this gold standard which has essentially yielded limited data and has highlighted the challenges in substantiating the therapies true benefits, side effects, etc.

The fundamental underlying advantage that the 90I novel molecule has in comparison to the current treatments used for COVID-19 may include multiple mode of action that parallels to not one, but all currently used treatments (antimalarial, anti-HIV protease inhibitors, and interferon), highly active (HAART), proven effective against resistance, such that promoting use of this drug without the need of combinatorial drugs being required, a natural product, provides a boost to the immune system, reverse latent infection, highly effective in brain cells, non toxic, and affordable.

Described below is an in silico analysis of 90I when comparing it to other control drugs that are in phase III, namely chloroquine phosphate, hydroxychloroquine, Remdesivir, and LPV/RTV.

In vitro results of 90I may yield a high Therapeutic Index, excellent EC50, and IC50 against HIV, as discussed above. Moreover, a toxicity test may be performed for safety assessment issues and risks for humans, identified through hepatotoxicity (i.e. chemical-driven liver damage), genotoxicity (i.e. chemical information that damages the genetic information within a cell causing mutations), immunogenicity (i.e. ability of a foreign substance, such as an antigen, to provoke an immune response in the body of a human or other animal), general toxicology, nephrotoxicity (i.e. renal toxicity occurs when a drug or toxin damages the kidneys), and secondary drug metabolite pharmacology studies.

A toxicity protocol may be utilized to assess COVID-19 safety, such that the toxicity protocol was already designed prior to the COVID-19 pandemic and established for HIV and the other infectious diseases under investigation. Also, many of the issues previously noted for current COVID-19 therapies by evaluating thoroughly the 90I compound in response to contact with a biological system. Previous therapies failed to analyze the biological responses, such as inhibition of key enzymes, interaction with receptors, interaction with other therapies patients received, etc.

Each of the current therapies noted above, chloroquine phosphate, hydroxychloroquine, Remdesivir, and LPV/RTV, were used in parallel comparison analysis utilizing virtual screening based on prediction (See https://www.researchgate.net/publication/339812164_Virtual_Screening_Based_Prediction_of_Potential_Drugs_for_COVID-19).

Please refer to Table 2 below for a summary of current therapy auto dock results.

TABLE 2

| Potential Drug | Status | Vina score | SMINA score | Dissociation Constant | Category | Approved for | Experimental |
|---|---|---|---|---|---|---|---|
| Ritonavir | Phase 4 | −7.5 | −7.7 | 2.5E−06 | Protease inhibitor | HIV/AIDS | |
| Lopinavir | Phase 4 | −7.4 | −7.5 | 3.4E−06 | Protease inhibitor | HIV/AIDS | |
| Umifenovir | Phase 4 | −6.4 | −6.0 | 2.2E−05 | Protease inhibitor | Influenza | |
| Methylprednisolone | Phase 4 | −7.8 | −7.6 | 2.1E−06 | Immunomodulator | Rheumatism/allergy | |
| Remdesivir | Phase 3 | −7.5 | −7.6 | 3.1E−06 | RNA polymerase inhibitor | | Ebola and Marburg |
| Cobicistat | Phase 3 | −7.2 | −7.2 | 5.7E−06 | Cytochrome P450 CYP3A inhibitor | HIV/AIDS | |
| Thalidomide | Phase 2 | −7.0 | −6.3 | 7.9E−06 | Immunosuppresive and Antiangiogenic | ENL | |
| Ribavirin | Phase 2 | −6.3 | −6.6 | 1.6E−05 | RNA-dependent RNA polymerase inhibitor | Hepatitis C | |
| Oseltamivir | Phase 4 | −6.5 | −6.3 | 1.8E−05 | Sialidase inhibitor | Influenza | |
| Hydroxychloroquine | Phase 3 | −6.0 | −6.4 | 2.3E−05 | Endosomal acidification fusion inhibitor | Malaria | |
| Chloroquine | Phase 4 | −5.9 | −5.4 | 5.0E−05 | Endosomal acidification fusion inhibitor | Malaria | |
| Fingolimod | Phase 2 | −5.9 | −5.6 | 5.0E−05 | Sphingosin 1-phosphate receptor modulator | Multiple sclerosis | |

Figure 5:
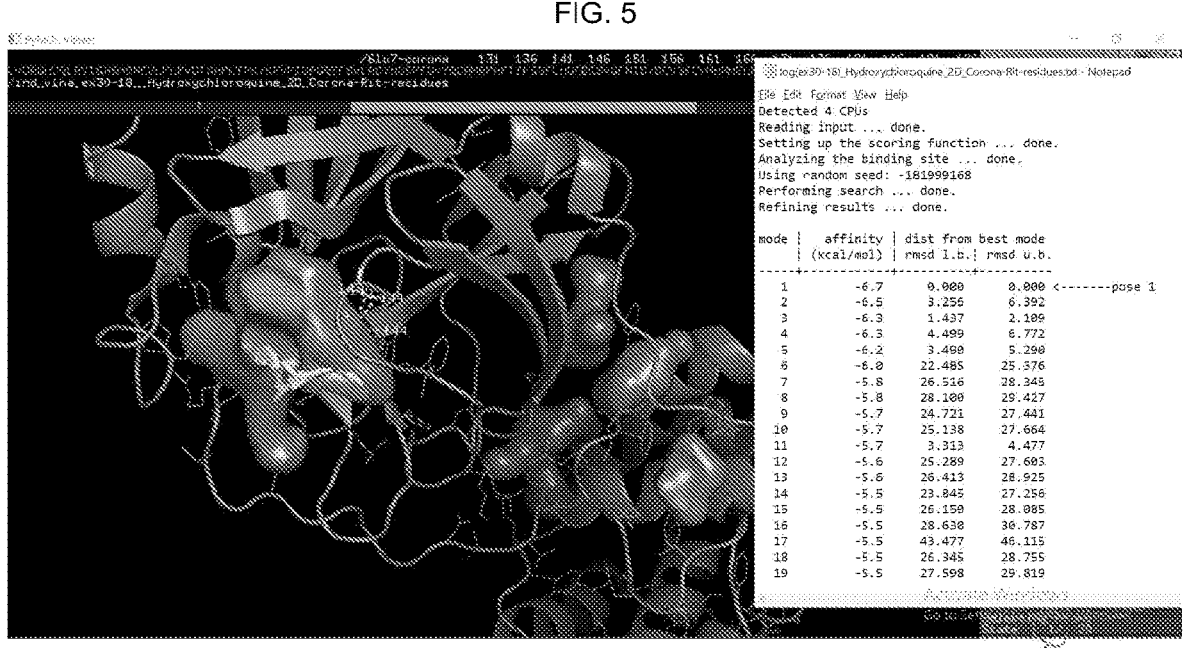
FIG. 5 illustrates Hydroxychloroquine interacting with residues, H41 and C145.
Figure 6:
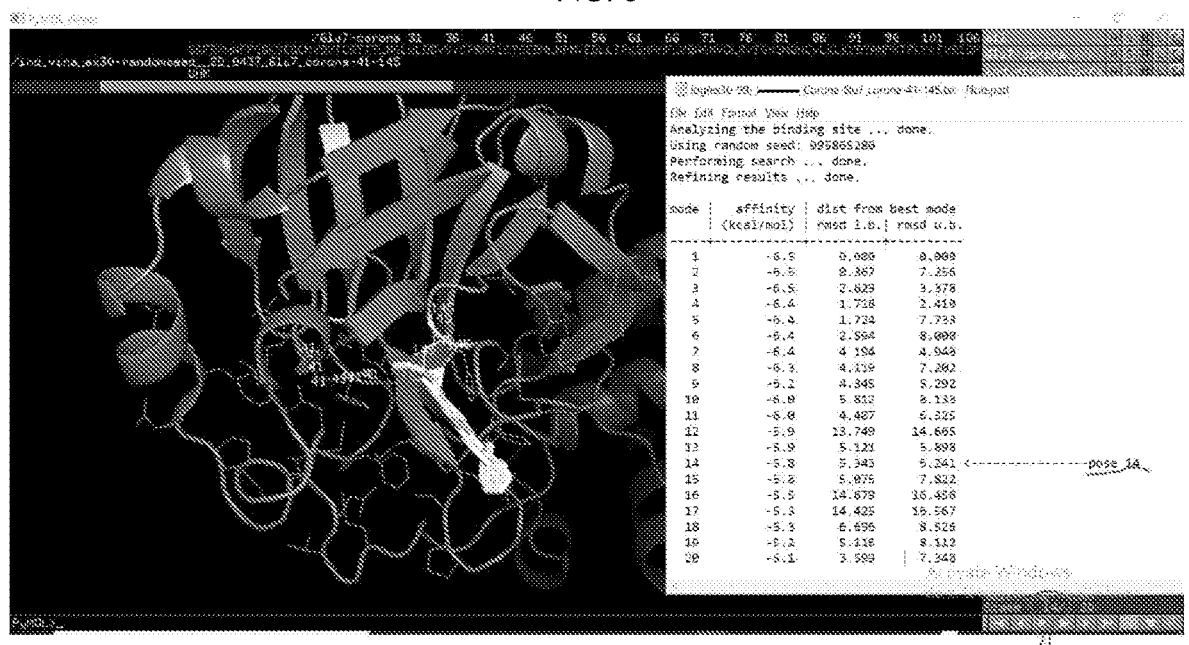
FIG. 6 illustrates 90I at −6.5 kcal/mol, according to an exemplary embodiment of the present general inventive concept.
Figure 7:
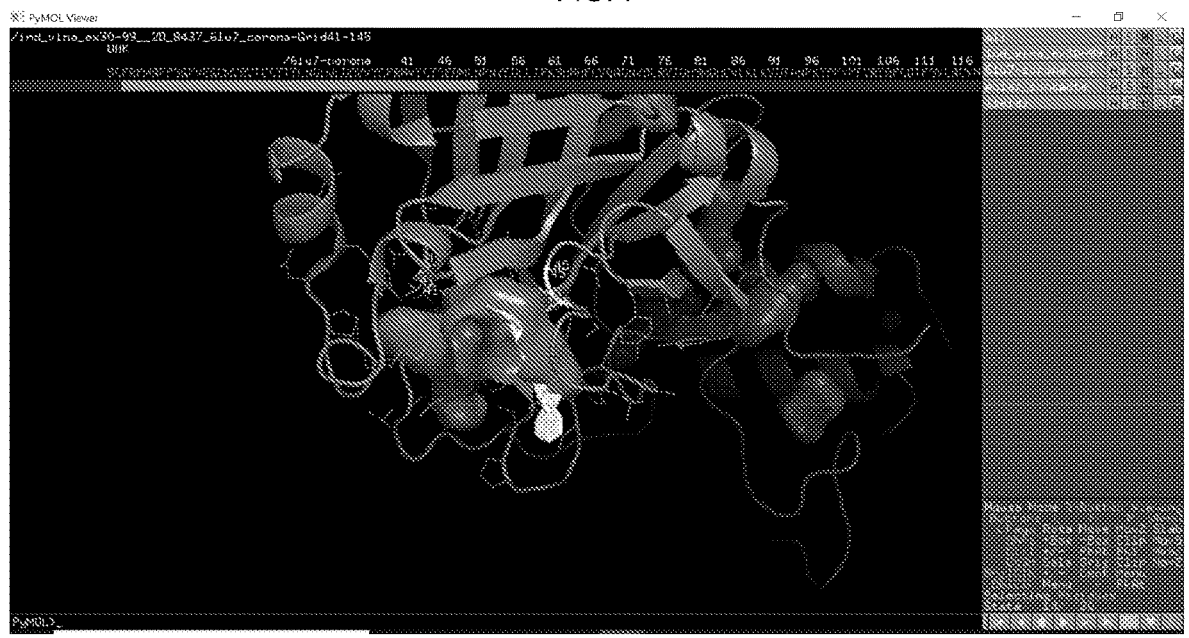
FIG. 7 illustrates a position of the 90I molecule right at the residues of the residue binding domain (RBD) pocket, according to an exemplary embodiment of the present general inventive concept.
Figure 8:
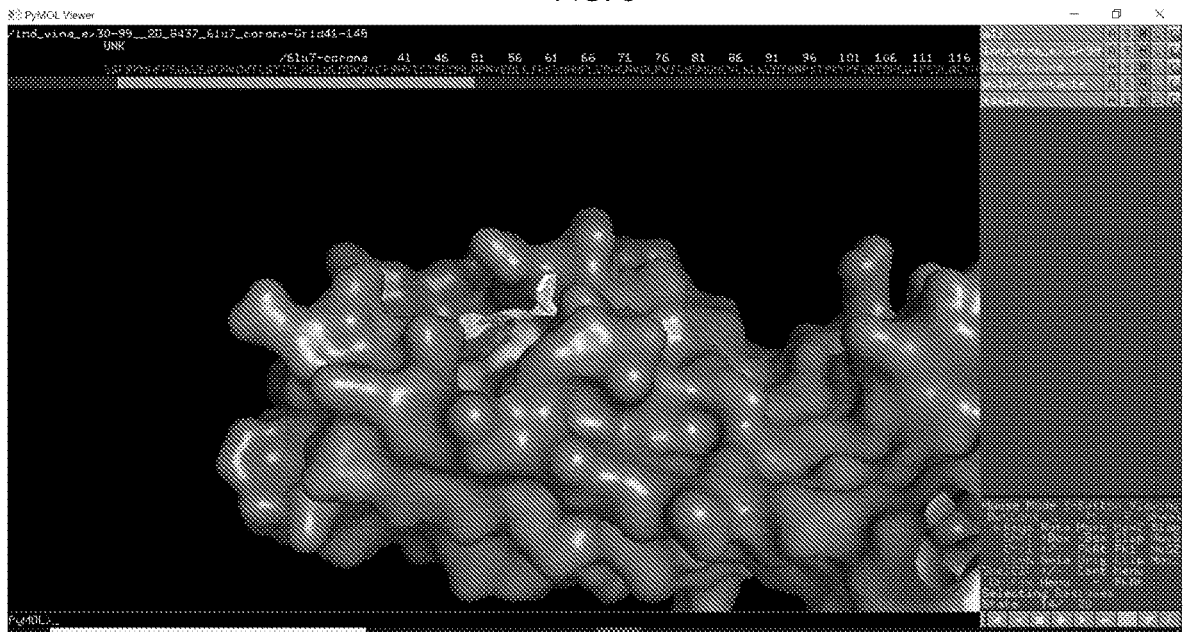
FIG. 8 illustrates a surface image of a protease and 90I sitting right at the pocket including a hydrogen (H) bond as a blue dotted line, during interaction with the residues, pose fourteen, according to an exemplary embodiment of the present general inventive concept.
Figure 9:
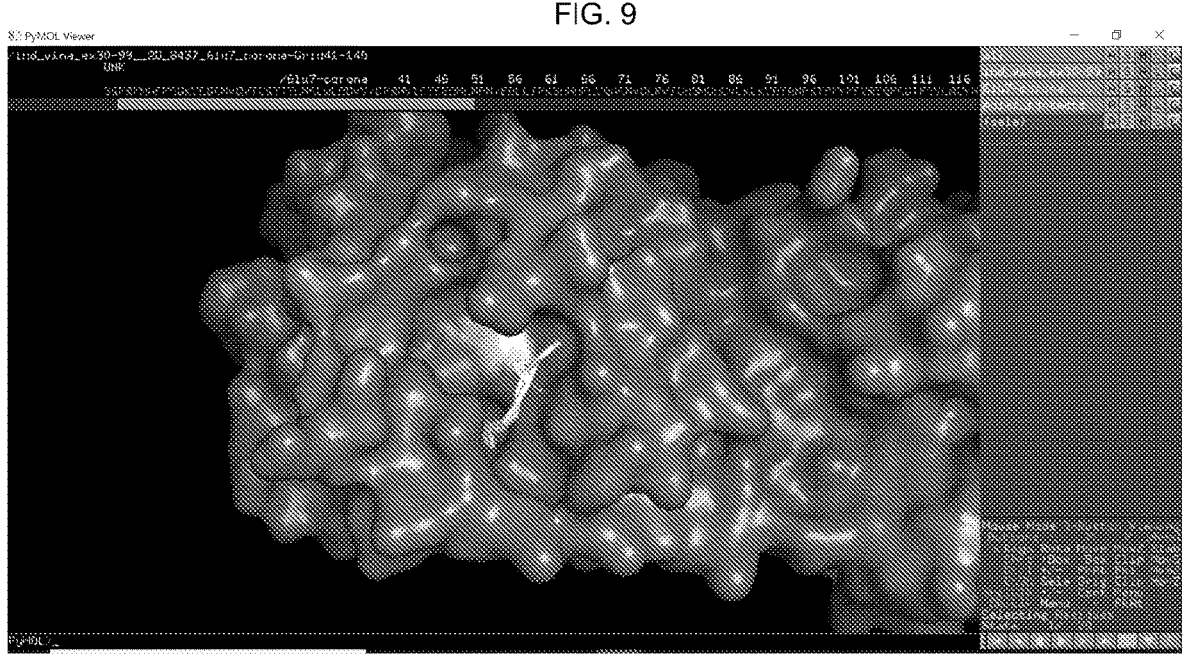
FIG. 9 illustrates another surface image of 90I on a first pose, according to an exemplary embodiment of the present general inventive concept.
Figure 10:
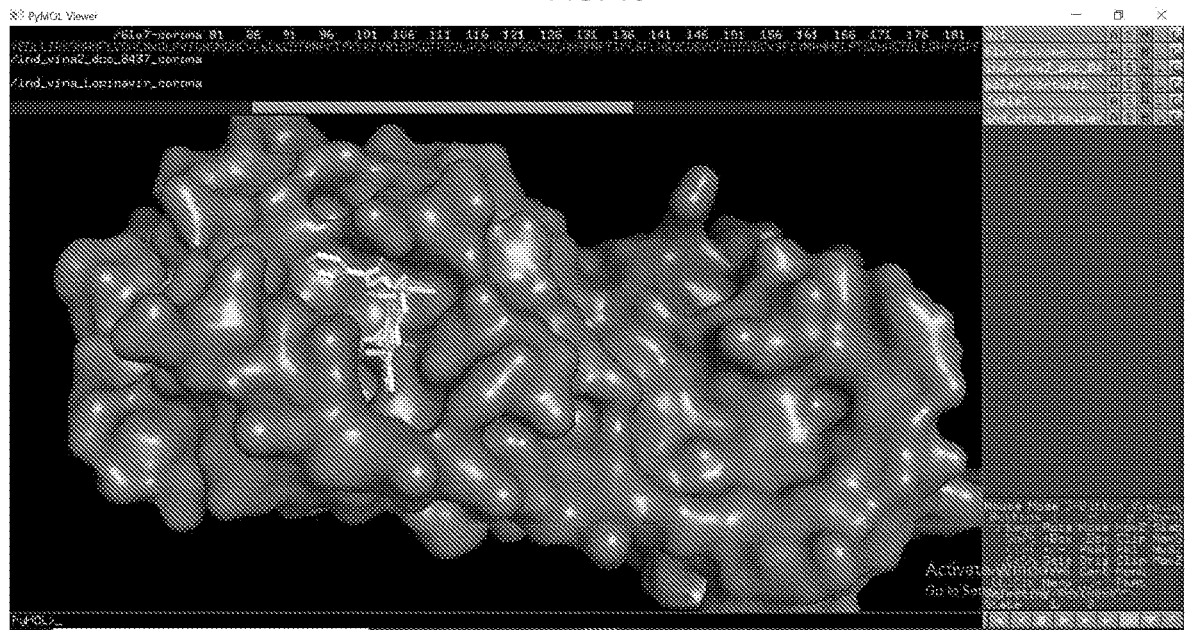
FIG. 10 illustrates the first pose surface view of 90I in white and Lopinavir in green landing at a same pocket interacting similarly with the H bond in dotted lines, according to an exemplary embodiment of the present general inventive concept.
Figure 11:
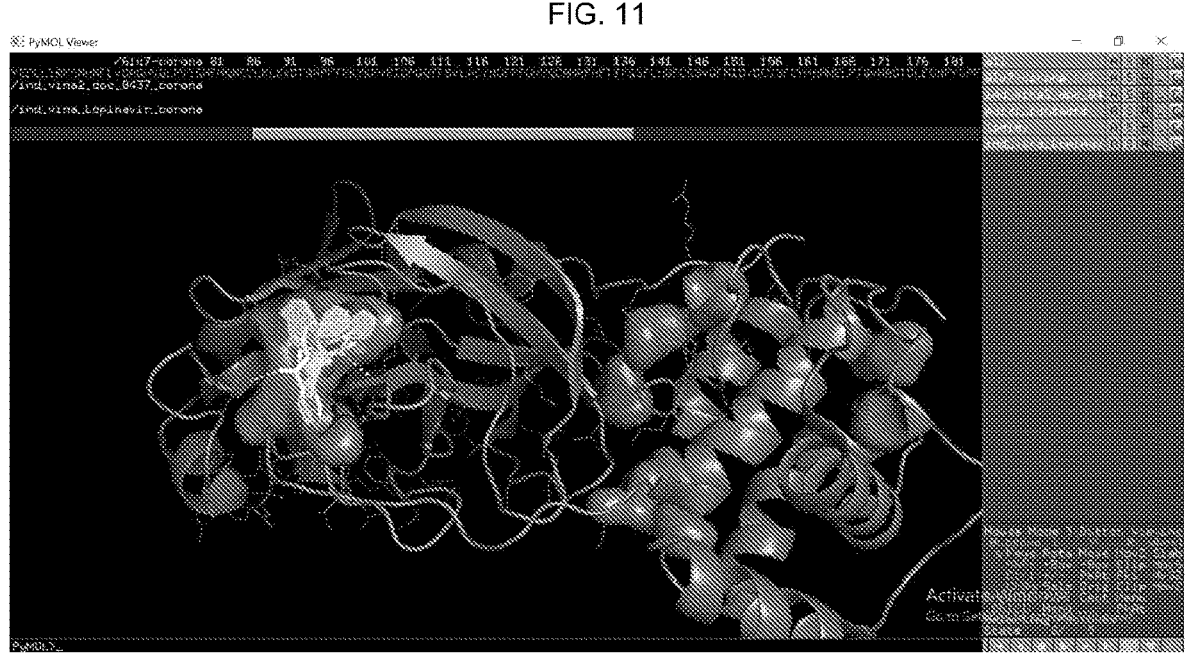
FIG. 11 illustrates a sixth pose of 90I in white and Lopinavir in green landing at the same pocket interacting similarly with the H bond in dotted lines, according to an exemplary embodiment of the present general inventive concept.
Figure 12:
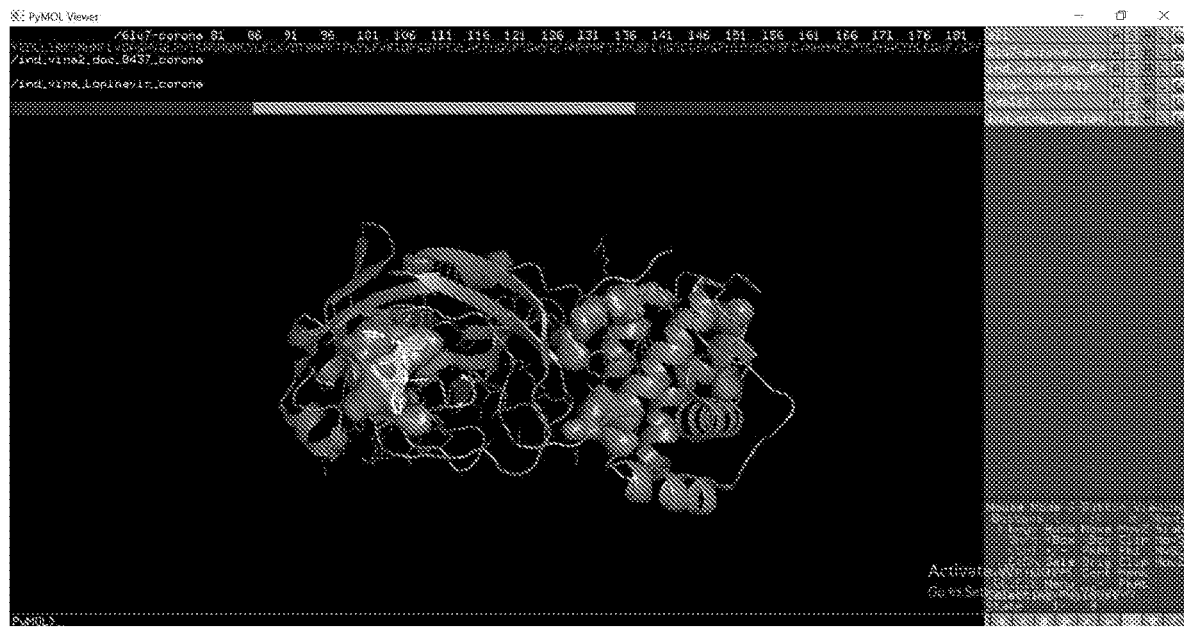
FIG. 12 illustrates the first pose surface view of 90I in white and Lopinavir in green landing at the same pocket interacting similarly with the H bond in dotted lines, according to an exemplary embodiment of the present general inventive concept.

FIG. 5 illustrates Hydroxychloroquine interacting with residues, H41 and C145.

Referring to FIG. 5 and Table 2, hydroxychloroquine was used as a control to compare it with 90I since hydroxychloroquine is in clinical trial phase III as a promising drug against SARS-CoV-2 (See http://clinicaltrial.org). Hydroxychloroquine shares the same number of carbon as 90I.

90I may interact with a host of other residues as shown in Table 3 below.

The results show hydroxychloroquine has −6.7 kcal/mol and hydrogen bond (H bond) of less than 3 Argon root-mean-square deviation (RSMD) to be an ideal distance from the residue atom that interacts to create a hydrogen bond.

According to previous studies found in peer-reviewed literature, there may be more significance of binding with a protein-ligand complex and having the lowest energy, such that there is a better binding affinity (i.e. strength of the binding interaction between a single biomolecule (e.g., a protein or DNA) to its ligand/binding partner (e.g., drug or inhibitor)). Moreover, a benchmark being 5 kcal/mol or less is better. The unit 5 kcal/mol is a unit used to measure how much energy was used to bind. The unit −5 kcal/mol is a maximum energy threshold to be considered a good drug candidate. Less than −5 kcal/mol means lesser energy was used. The lesser the kcal/mol the better. Testing results demonstrates the ligand can bind efficiently. The log results show that 90I binds to the key residues comparatively or better to the control drugs previously described as potential COVID-19 treatments.

FIG. 6 illustrates 90I at −6.5 kcal/mol, according to an exemplary embodiment of the present general inventive concept.

As mentioned previously, a binding with a protein-ligand complex and having the lowest energy, results in a better binding affinity. The benchmark is 5 kcal/mol or less is better, and an H bond of less than 3 Argon (RSMD) to be an ideal distance from the residue atom that interacts to create a hydrogen bond. There are at least six poses of H bond causing poses. The H bonds interact with the residues binding domain.

FIG. 7 illustrates a position of the 90I molecule right at the residues of the residue binding domain (RBD) pocket, according to an exemplary embodiment of the present general inventive concept.

FIG. 8 illustrates a surface image of a protease and 90I sitting right at the pocket including a hydrogen (H) bond as a blue dotted line, during interaction with the residues, pose fourteen, according to an exemplary embodiment of the present general inventive concept.

FIG. 9 illustrates another surface image of 90I on a first pose, according to an exemplary embodiment of the present general inventive concept.

LPV provides the same results, which is also in clinical trials. In other words, LPV has passed all of the in vitro tests.

FIG. 10 illustrates the first pose surface view of 90I in white and Lopinavir in green landing at a same pocket interacting similarly with the H bond in dotted lines, according to an exemplary embodiment of the present general inventive concept.

FIG. 11 illustrates a sixth pose of 90I in white and Lopinavir in green landing at the same pocket interacting similarly with the H bond in dotted lines, according to an exemplary embodiment of the present general inventive concept.

FIG. 12 illustrates the first pose surface view of 90I in white and Lopinavir in green landing at the same pocket interacting similarly with the H bond in dotted lines, according to an exemplary embodiment of the present general inventive concept.

The following table, Table 3, is followed by an in silico test showing 90I interacting with the binding sites shown in the table. See https://www.ncbi.nlm.nih.gov/pmc/articles/PMC7126105/.

Binding pocket for SARS-CoV main protease with different drugs. 90I does interact with all of the common denominator residues. All of the 140's, 180's, and more in addition to H41 and C145.

TABLE 3

Table 1. Binding pockets for SARS-Cov main proteinase with different drugs

| Lopinavir | Ritonavir | | Niclosamide | Promazine | PNU | UC2 |
|---|---|---|---|---|---|---|
| ARG 40 | GLN 19 | SER 123 | ARG 40 | ARG 40 | ARG 40 | HIS 41 |
| CYS 44 | VAL 20 | PHE 140 | MET 49 | ILE 43 | HIS 41 | MET 49 |
| MET 49 | THR 21 | LEU 141 | LEU 50 | CYS 44 | ILE 43 | LEU 50 |
| LEU 50 | CYS 22 | ASN 142 | ASN 51 | MET 49 | CYS 44 | ASN 51 |
| ASN 51 | GLY 23 | GLY 143 | PRO 52 | LEU 50 | MET 49 | HIS 164 |
| PRO 52 | THR 24 | SER 144 | ASN 53 | ASN 51 | LEU 50 | MET 165 |
| ASN 53 | THR 25 | CYS 145 | TYR 54 | PRO 52 | ASN 51 | GLU 166 |
| TYR 54 | THR 26 | GLY 146 | GLU 55 | ASN 53 | PRO 52 | LEU 167 |
| GLU 55 | LEU 27 | SER 147 | ASP 56 | TYR 54 | ASN 53 | PRO 168 |
| ASP 56 | ASN 28 | HIS 163 | LEU 57 | GLU 55 | TYR 54 | THR 169 |
| LEU 57 | PRO 39 | HIS 164 | MET 82 | ASP 56 | GLU 55 | GLY 170 |
| MET 82 | ARG 40 | MET 165 | VAL 186 | LEU 57 | ASP 56 | VAL 171 |
| ASN 84 | HIS 41 | GLU 166 | ASP 187 | LEU 58 | LEU 57 | HIS 172 |
| CYS 85 | VAL 42 | LEU 167 | ARG 188 | MET 82 | LEU 58 | ALA 173 |
| PHE 181 | ILE 43 | PRO 168 | GLN 189 | ASN 84 | MET 82 | PHE 181 |
| PHE 185 | CYS 44 | VAL 171 | THR 190 | CYS 85 | GLN 83 | PRO 184 |
| VAL 186 | MET 49 | HIS 172 | | VAL 186 | ASN 84 | PHE 185 |
| ASP 187 | LEU 50 | ALA 173 | | ASP 187 | CYS 85 | VAL 186 |
| ARG 188 | ASN 51 | GLY 174 | | ARG 188 | LEU 86 | ASP 187 |
| GLN 189 | PRO 52 | PHE 181 | | GLN 189 | VAL 186 | ARG 188 |
| THR 190 | ASN 53 | PHE 185 | | THR 190 | ASP 187 | GLN 189 |
| ALA 191 | TYR 54 | VAL 186 | | | ARG 188 | THR 190 |
| GLN 192 | LEU 57 | ASP 187 | | | GLN 189 | ALA 191 |
| | CYS 117 | ARG 188 | | | THR 190 | GLN 192 |
| | TYR 118 | GLN 189 | | | | ALA 193 |
| | ASN 119 | THR 190 | | | | ALA 194 |
| | GLY 120 | ALA 191 | | | | |
| | SER 121 | GLN 192 | | | | |
| | | ALA 193 | | | | |

Figure 13A:
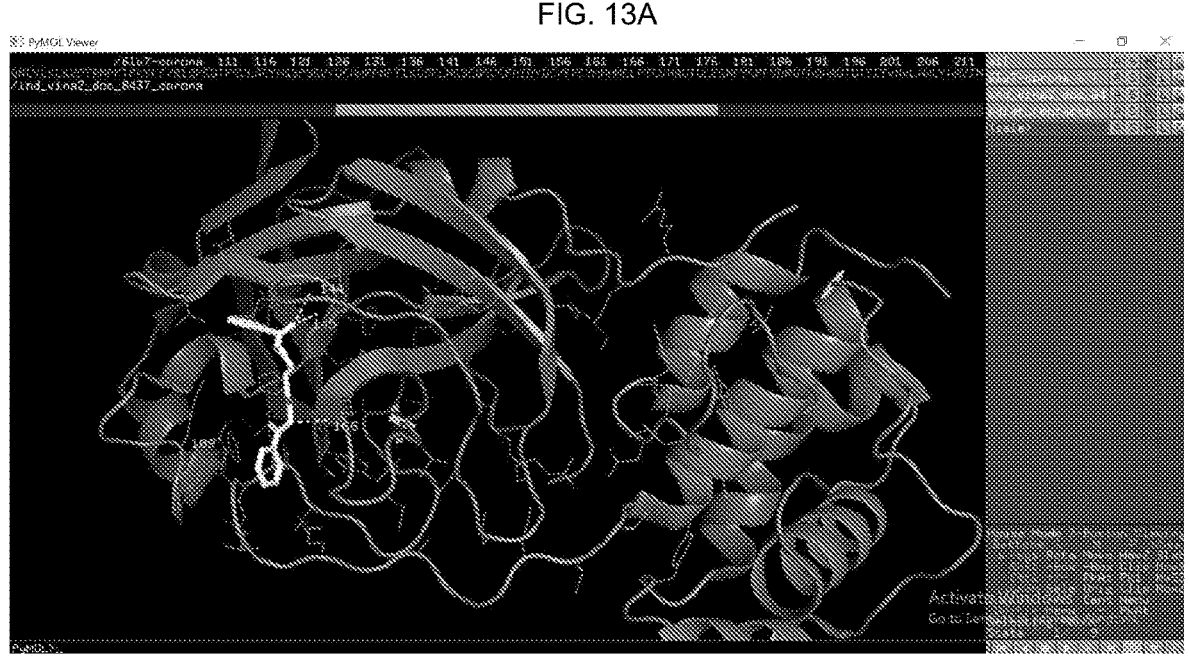
FIG. 13A illustrates 90I interacting with residues CER 144 (cerium 144), CYS 145 (cysteine 145), GLN 189 and GLU 166 (glutamate 166), according to an exemplary embodiment of the present general inventive concept.

FIG. 13A illustrates 9OI interacting with residues CER 144 (cerium 144), CYS 145 (cysteine 145), GLN 189 and GLU 166 (glutamate 166), according to an exemplary embodiment of the present general inventive concept.

Figure 13B:
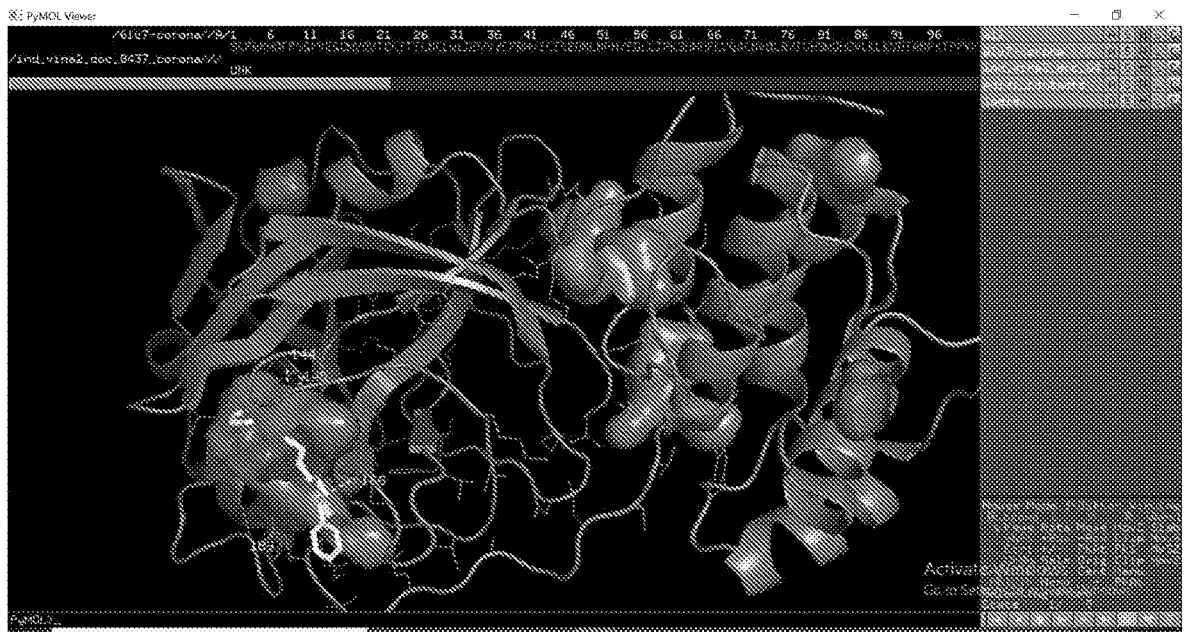
FIG. 13B illustrates 90I interacting with residues CER 144 (cerium 144), CYS 145 (cysteine 145), GLN 189 and GLU 166 (glutamate 166), according to an exemplary embodiment of the present general inventive concept.

FIG. 13B illustrates 9OI interacting with residues CER 144 (cerium 144), CYS 145 (cysteine 145), GLN 189 and GLU 166 (glutamate 166), according to an exemplary embodiment of the present general inventive concept.

Figure 13C:
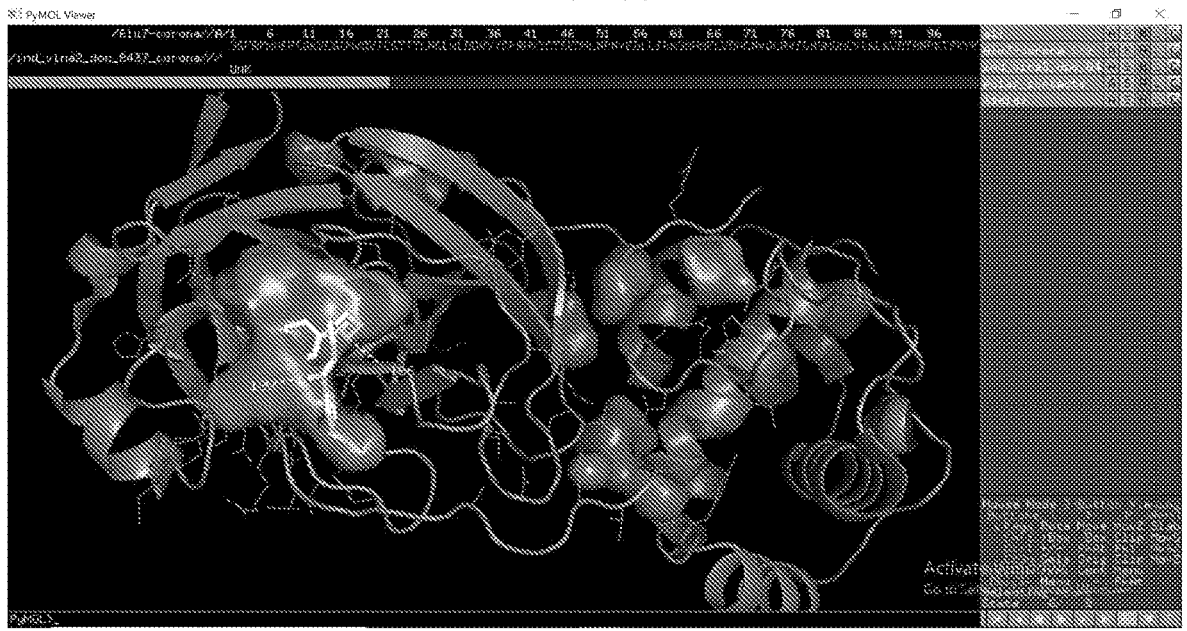
FIG. 13C illustrates 90I interacting with residues CER 144 (cerium 144), CYS 145 (cysteine 145), GLN 189 and GLU 166 (glutamate 166), according to an exemplary embodiment of the present general inventive concept.

FIG. 13C illustrates 9OI interacting with residues CER 144 (cerium 144), CYS 145 (cysteine 145), GLN 189 and GLU 166 (glutamate 166), according to an exemplary embodiment of the present general inventive concept.

Figure 14A:
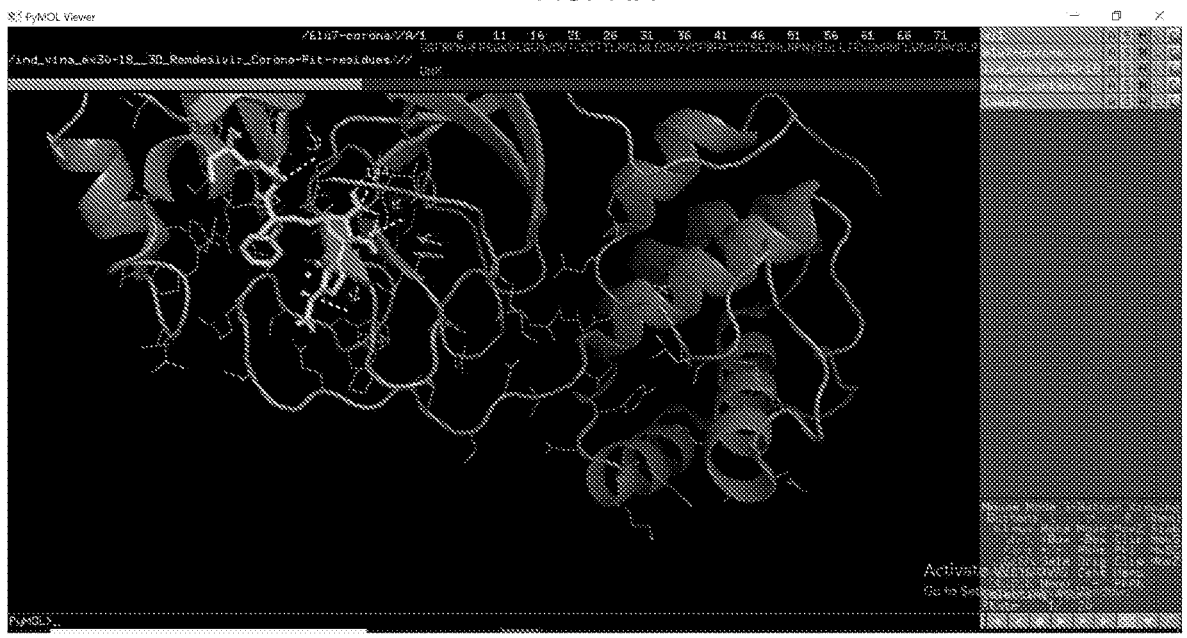
FIG. 14A illustrates Remdisavir interacting with residue CER 144.

FIG. 14A illustrates Remdesivir interacting with residue CER 144.

Referring to FIG. 14A, Hydrogen bonds are in red, but no residues are affected. 9OI may interact with more residues. Although, Remdesivir is a nucleoside analog, it shows interaction with MProtease. Moreover, 9OI may also act as a nucleoside analog, as it was compared to AZT.

Figure 14B:
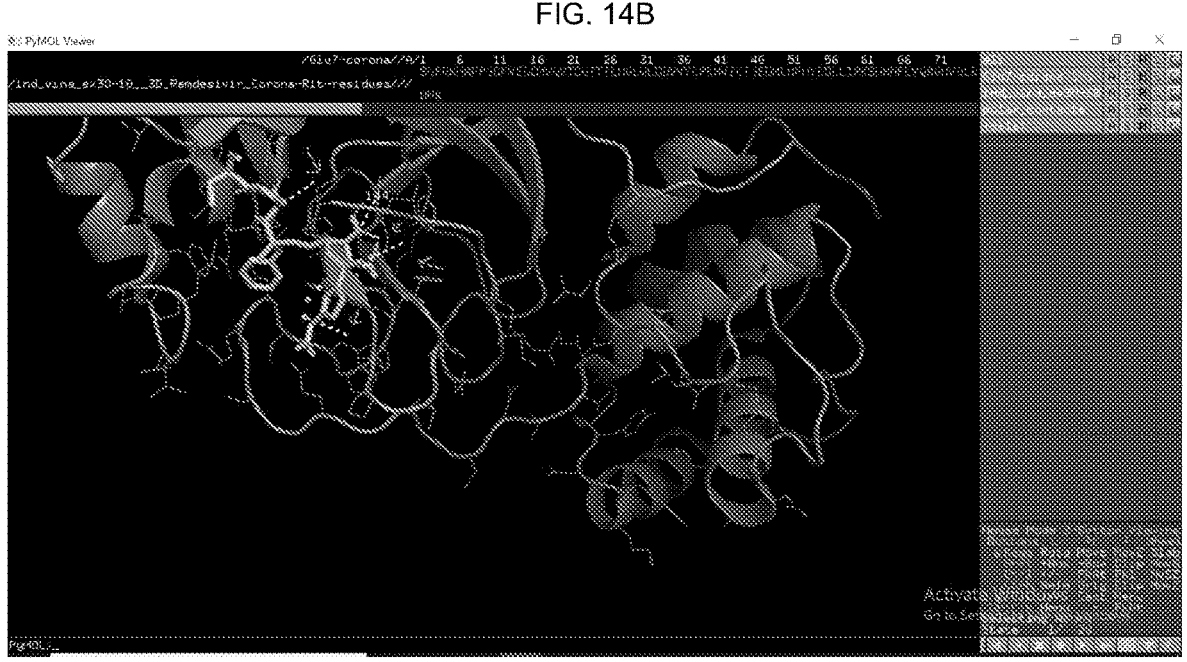
FIG. 14B illustrates Remdisavir interacting with residue CER 144, including a log file.

FIG. 14B illustrates Remdesivir interacting with residue CER 144, including a log file.

Referring to FIG. 14B, only the first and second pose have short distance of less than 3.5 A, but in this case, both show zero. Compared to Remdesivir, 9OI is a far better molecule because it not only has lots of scores when it comes to a short distance that is less than 3.5 argon RMSD, but 9OI may also exhibit very low kcal/mol at those distances implying less energy consumed to dock to the receptors in question. As such, 9OI may be very good biologically since not much energy is consumed. Also, 9OI may consume as much energy as Remdisavir, but has more close encounters with the residues as shown in 9OI's log where it shows multiple times less kcal/mol, and less than 3.5 Argon RMSD distance between the 9OI molecule and the atoms of the residues.

Figure 15:
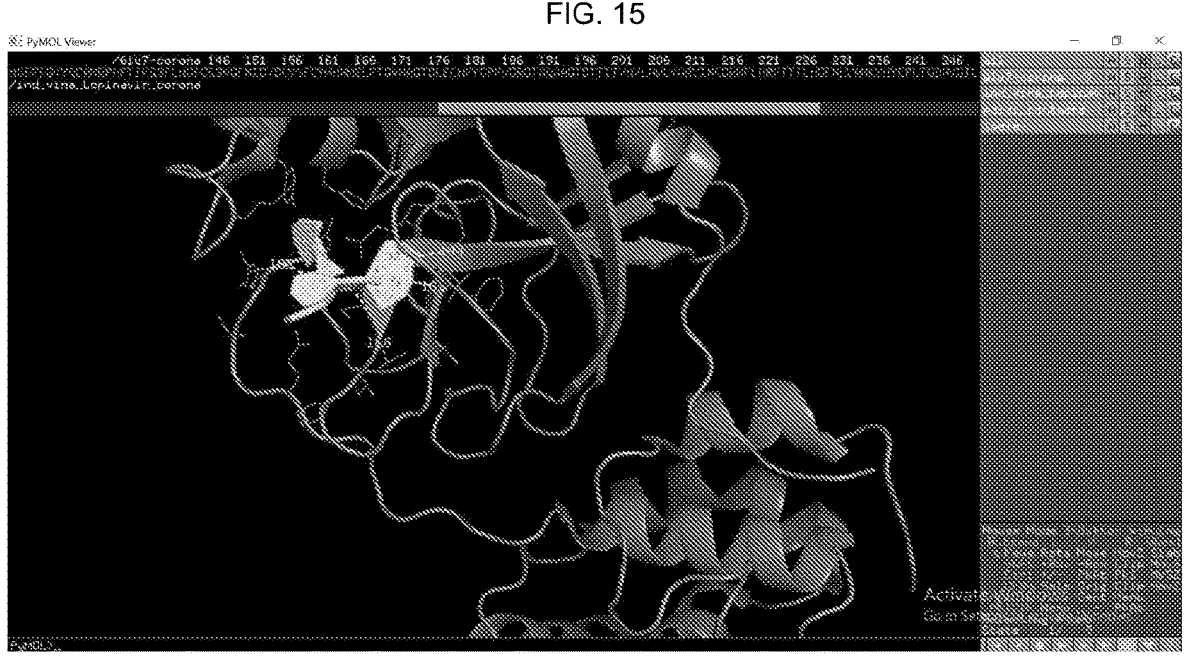
FIG. 15 illustrates Lopinavir interacting with residues CER 144 (cerium 144), CYS 145 (cysteine 145), GLN 189 and GLU 166 (glutamate 166)

FIG. 15 illustrates Lopinavir interacting with residues CER 144 (cerium 144), CYS 145 (cysteine 145), GLN 189 and GLU 166 (glutamate 166).

SARS-CoV-2 Assay

Similar to 9OI's in vitro success on HIV, thereby confirming 9OI's biological significance, further in vitro tests may be necessary using a biosafety level (BSL) 3 lab for SARS-CoV-2, which is arranged. The result is expected within a month. The in vitro assays will include Vero (i.e. a lineage of cells used in cell culture) or Huh7 (i.e. a type of human liver cell that may be grown in a laboratory for research purposes) cell line and also MProtease (SARS-CoV-2 main protease). The assay will then test for EC50, Therapeutic Index, and 1050, as well as equilibrium dissociation (KD) constant (i.e. equilibrium disassociation constant measures binding affinity, which is used to evaluate and rank order strengths of bimolecular interactions). The results will be available in a month to two months.

Initial screening is normally done using a neutral red assay to evaluate inhibition of viral-induced cytopathic effects (CPE). Active compounds may then be tested using a virus yield reduction (VYR) assay.

Test #2

Virus: HCoV

Cell line: Huh7

Detection reagent: CellTiter Glo

Reference: Remdesivir or chloroquine phosphate

Treatment duration: 4 days

Format: 96 well

Remdesivir, EC50=0.0064 uM, CC50=28.95 uM

Chloroquine phosphate 3.45, 40.83

Test #3

Spike pseudovirus: assay

Virus: COVID-19 S pseudovirus

Cells: HEK293/ACE-2, Huh7 or Vero

Treatment: pre-incubation of pseudovirus with compounds, then incubation with cells for 3 days Detection reagent: luciferase assay kit No Control Test #4

Mpro enzymatic assay

Mpro and Substrate

Enzymatic reaction time: 40 min

Assay window: ~6 folds

Format: 384 well

Z factor: 0.7

Lopinavir, EC50=108 uM

Ritonavir, EC50=293 uM

Therefore, the discovery of a method and compound for treatment of COVID-19, such that SARS-CoV-2 may be cured may save the world and society from collapsing.

REFERENCES

The following reference(s) may provide exemplary procedural and/or other details supplementary to those set forth herein, and are specifically incorporated herein by reference.

Effect of High vs Low Doses of Chloroquine Diphosphate as Adjunctive Therapy for Patients Hospitalized With Severe Acute Respiratory Syndrome Coronavirus 2 (SARS-CoV-2) Infection, Mayla Gabriela Silva Borba, MD; Fernando Fonseca Almeida Val, PhD; Vanderson Souza Sampaio, PhD; et al, JAMA.

"Trial of chloroquine to treat COVID-19 stopped early due to heart complications", LiveScience, By Rachael Rettner.

Lopinavir/Ritonavir: A rapid review of effectiveness in COVID-19. https://www.cebm.net/covid-19/lopinavir-ritonavir-a-rapid-review-of-the-evidence-for-effectiveness-in-treating-covid.

Remdesivir for COVID Study: Benefits Not Clear, https://www.webmd.com/lung/news/20200414/remdesivir-for-covid-study-benefits-not-clear.

New data on Gilead's remdesivir, https://www.statnews.com/2020/04/23/data-on-gileads-remdesivir-released-by-accident-show-no-benefit-for-coronavirus-patients.

Remdesivir and chloroquine effectively inhibit the recently emerged novel coronavirus (2019-nCoV) in vitro, https://www.nature.com/articles/s41422-020-0282-0.

Chloroquine is a potential inhibitor of SARS coronavirus infection and spread, https://www.ncbi.nlm.nih.gov/pmc/articles/PMC1232869/.

Potential inhibitors for 2019-nCoV coronavirus M protease from clinically approved medicines, https://www.biorxiv.org/content/10.1101/2020.01.29.924100v1.full.

Why are Lopinavir and Ritonavir Effective against the Newly Emerged Coronavirus 2019?, https://www.ncbi.nlm.nih.gov/pubmed/32293875.

Role of lopinavir/ritonavir in the treatment of SARS: initial virological and clinical findings, https://www.ncbi.nlm.nih.gov/pubmed/14985565. Also, https://www.researchgate.net/publication/7259304_Role_of_lopinavir-ritonavir_in_the_treatment_of_SARS_initial_virological_and_clinical_findings.

Virtual Screening Based Prediction of Potential Drugs for COVID-19, https://www.researchgate.net/publication/339812164_Virtual_Screening_Based_Prediction_of_Potential_Drugs_for_COVID-19.

Old drugs as lead for compounds for new disease?, https://www.ncbi.nlm.nih.gov/pmc/articles/PMC7126105/.
Effectiveness of Hydroxychloroquine in Covid-19 Patients, https://clinicaltrials.gov/ct2/show/NCT04328272.
Study to Evaluate the Safety and Antiviral Activity of Remdesivir (GS5734™) in Participants with Severe Coronavirus Disease (COVID-19), https://clinicaltrials.gov/ct2/show/NCT04292899.
COVID-19 Ring-based Prevention Trial With Lopinavir/Ritonavir (CORIPREV-LR), https://clinicaltrials.gov/ct2/show/NCT04321174.

The present general inventive concept may include a method for the treatment of a coronavirus disease, including administering to a subject in need thereof of an anti-pathogenic compound, such that the anti-pathogenic compound is derived from an herbal extract.

The herbal extract may be a glycol derivative.

The glycol derivative may be diethylene glycol dibenzoate.

The coronavirus disease may be COVID-19.

The present general inventive concept may also include a method of strengthening a subject infected with a coronavirus disease, including administering to the subject in need thereof of an anti-pathogenic compound, such that the anti-pathogenic compound is derived from an herbal extract.

The herbal extract may be a glycol derivative.

The coronavirus disease may be COVID-19.

The anti-pathogenic compound may boost an immune system of the subject.

Boosting the immune system may include revitalizing at least one of a dysfunctional monocyte and a dysfunctional macrophage.

Boosting the immune system may include stimulating production of gamma interferon.

Boosting the immune system may use only the anti-pathogenic compound, but is not limited thereto.

Preliminary In Vitro Findings of 90I Against SARS-CoV-2

Remdesivir was used as a control and verified that the assay was working. The first independent trial (done in quadruplicate) involved using the very first BTS compound sent to us, dissolved at 10 ug/ml in DMSO. Toxicity was observed ~0.078 ug/ml (~2.5 uM based on the molecular weight we were given and the concentration of the drug). The dose curve (log (inhibitor) vs. response (three parameters)) yielded the nicest curve, but only reached a maximum of ~20% protection. IC50 values were 0.0028 uM and the EC50 was 4.1 uM. Twenty-two 2-fold dilutions of the drug starting from 10 ug/ml (~323 uM).

Figure 16:
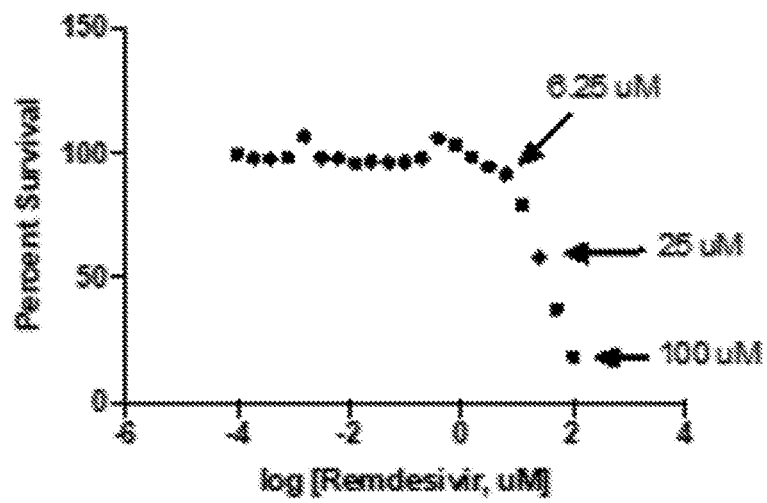
FIG. 16 illustrates a graph showing Remdesivir toxicity in Vero E6 cells.

FIG. 16 illustrates a graph showing Remdesivir toxicity in Vero E6 cells.

Figure 17:
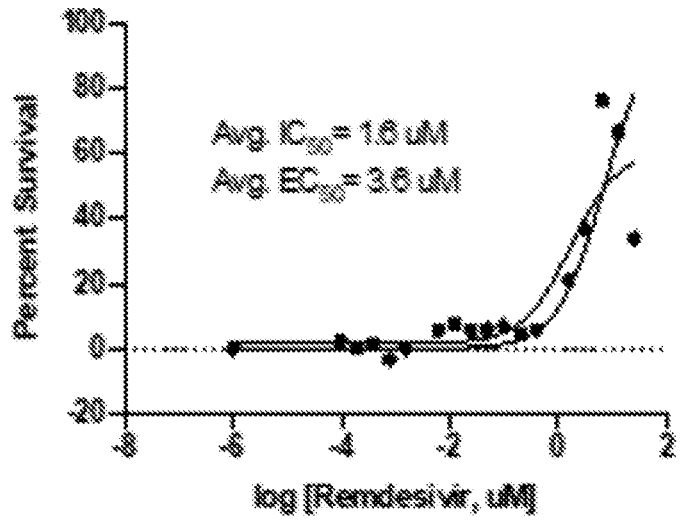
FIG. 17 illustrates a graph showing one hour pretreatment of Remdesivir applied to seventy-two hour SARS-CoV-2 infected cells.

FIG. 17 illustrates a graph showing one hour pretreatment of Remdesivir applied to seventy-two hour SARS-CoV-2 infected cells.

Figure 18:
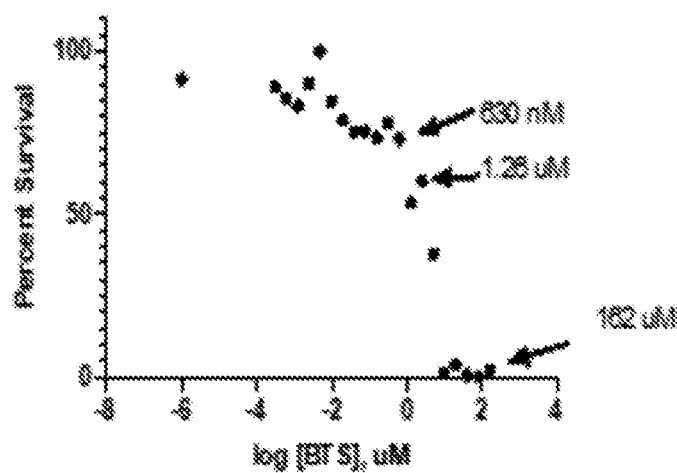
FIG. 18 illustrates a graph showing 90I toxicity in Vero E6 cells, according to an exemplary embodiment of the present general inventive concept.

FIG. 18 illustrates a graph showing 90I toxicity in Vero E6 cells, according to an exemplary embodiment of the present general inventive concept.

Figure 19:
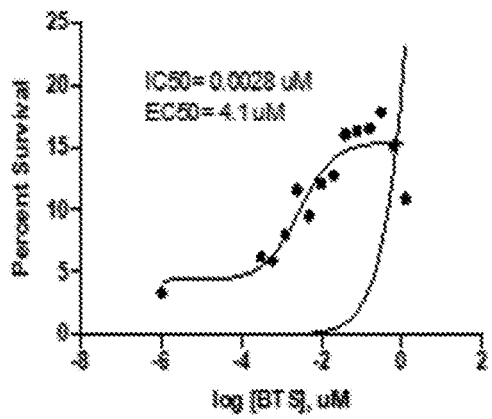
FIG. 19 illustrates a graph showing one hour pretreatment of 90I applied to seventy-two hour SARS-CoV-2 infected cells, according to an exemplary embodiment of the present general inventive concept.

FIG. 19 illustrates a graph showing one hour pretreatment of 90I applied to seventy-two hour SARS-CoV-2 infected cells, according to an exemplary embodiment of the present general inventive concept.

Bio-T Square is currently working on further development on diethylene glycol dibenzoate, also known as DEGD and/or 90I.

The initial synthesis/lab demonstration work is intended to provide material for (a) reference studies and (b) provide data on a synthesis GLP enabling tox studies. This initial synthesis will be run non-GMP (i.e. good manufacturing practice), but the documentation of the synthesis and analytical data will be of a standard to enable this material to be used for the GLP (i.e. good laboratory practice) enabling toxicity studies.

It is important to note that while DEGD has not had a formal Safebridge assessment, has significant toxicity data available in the public literature (as summarized in Appendix A below).

Figure 20:
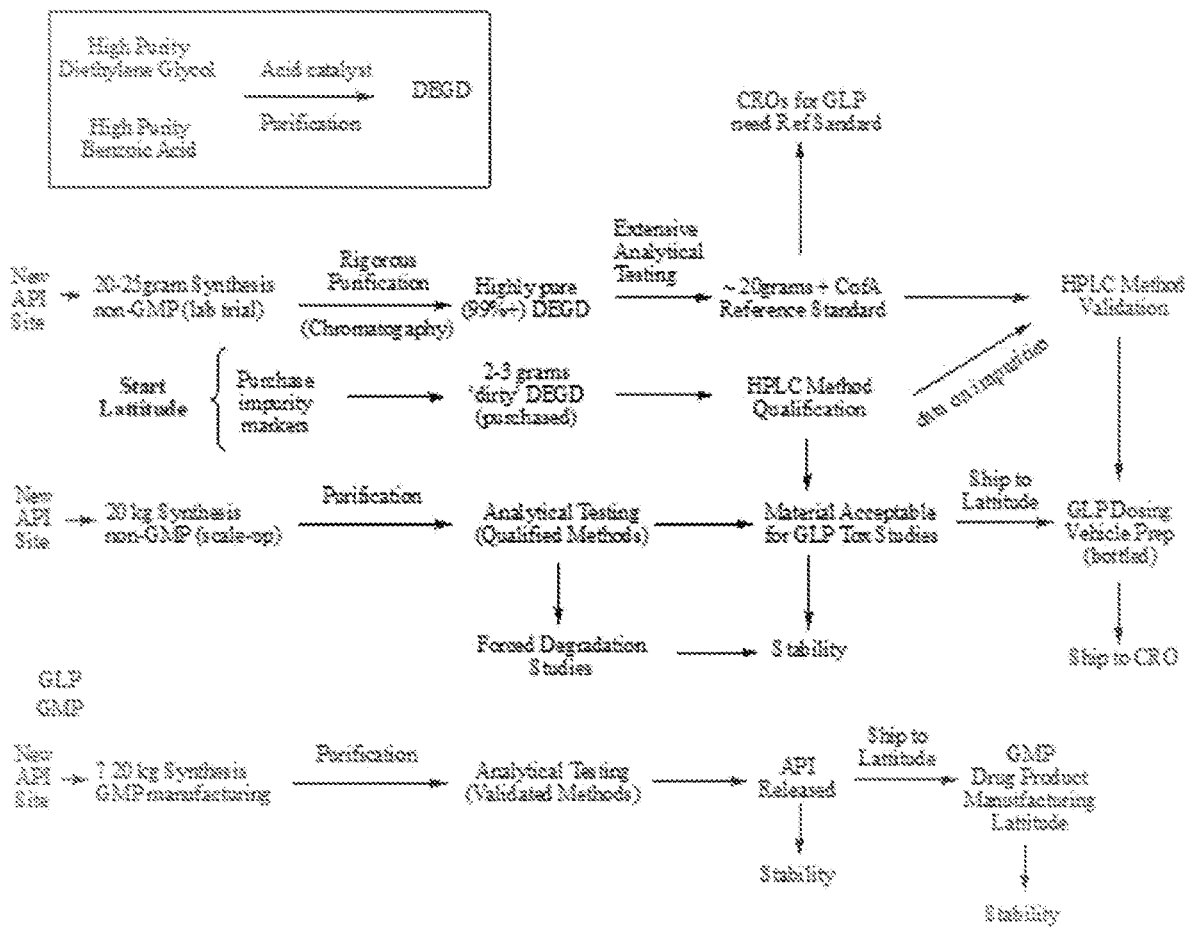
FIG. 20 illustrates an API development scheme.

FIG. 20 illustrates an API development scheme.

Section 1: Evaluation and Demonstration Synthesis

The goal of this section is to apply the synthesis to (a) demonstrate a scalable synthesis and (b) provide 10-20 g of DEGD (90I) for use as a Reference Standard material for future work. The recommended synthesis is illustrated in FIG. 21.

Figure 21:
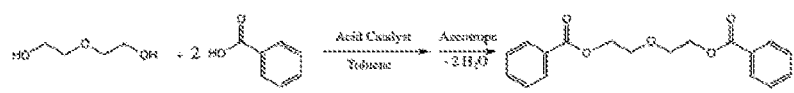
FIG. 21 illustrates a standard for synthesis of 90I, according to an exemplary embodiment of the present general inventive concept.

FIG. 21 illustrates a standard for synthesis of 90I, according to an exemplary embodiment of the present general inventive concept.

Section 2: Analytical—Development and Reporting

The following information is available in Appendix A: $^1$H NMR spectra; FTIR spectra; HPLC Method and representative spectra; Representative LC-MS spectra; and Solubility and physical property data.

The tests in this section 2 shall be performed in a GMP or GLP laboratory. The analytical data to be included on the reference standard and GLP batch Certificate of Analysis is detailed below.

Bio-T Square is currently working with J-star to reproduce the preliminary HPLC (i.e. high performance liquid chromatography) method provided to develop the HPLC analytical method(s) necessary for the release testing of the reference standard and GLP lot.

The current HPLC method has been run 220 nm. Care should be taken in the analysis as the diethylene glycol starting material has limited response at 220 nm. As part of the analytical work, a UV profile of the DEGD (90I) will be run.

Bio-T Square is working to establish the following: A Certificate of Analysis (CofA) with copies of all raw data used to generate the CofA for both the reference standard and the GLP lot; Copies of the analytical methods used; Copies of original spectra obtained; and Development reports for any optimization or development work.

A Certificate of Analysis (CofA) will be produced for both the reference standard and the GLP lot(s) of DEGD. The CofA testing should include the testing shown in below, using the analytical methods indicated. The tables below also include the proposed specification.

The following will be executed with the following tests on the 10 g synthesis (reference standard) materials:

TABLE 4

| TEST NAME | ACCEPTANCE LIMITS |
| --- | --- |
| Appearance (visual inspection) | Report |
| FT-IR USP <197> | Collect Representative Spectra* |
| HPLC | Retention time of main peak consistent with reference marker |
| Water content by USP <921> | Report |
| Residual Solvents | Report |
| Impurities by HPLC (HPLC area %) | Report - Target is Total impurities ≤1%** @220 nm |

TABLE 4-continued

| TEST NAME | ACCEPTANCE LIMITS |
|---|---|
| LC-MS | Report |
| $^1$H-NMR USP <761> | Consistent with structure |
| $^{13}$C-NMR USP <761> | Consistent with structure |
| Melting Point (DSC) | Report |
| TGA | Report |
| Elemental Analysis | C, H, O |
| UV by USP <851> | Collect 200 to 800 nm representative spectra |

Referring to Table 4, *Please collect using KBr pellet and **diethylene glycol has no active chromophore—HPLC-CAD may need to be used if 220 nm is insufficient to detect/quantify.

Section 3: Synthesis GLP Material

The goal of this section is to produce at least 20 kgs of DEGD, preferably as a single lot if possible, by the synthetic scheme(s) in Section 1 or following an improved process developed as a result of the work described in Section 1.

The starting material shall be diethylene glycol and/or benzoic acid and this material will be sourced by J-star. The DEGD (90I) should be tested to confirm absence of diethylene glycol to meet USP (i.e. United States Pharmacopeia) standards.

Bio-T Square Deliverables

The following tests will be executed on the GLP synthesis materials and create a CofA for the GLP batch:

TABLE 5

| TEST NAME | ACCEPTANCE LIMITS |
|---|---|
| Appearance (visual inspection) | Report |
| FT-IR USP <197> | Consistent with structure |
| HPLC (HPLC area %) | Retention time of main peak consistent with reference standard |
| Impurities by HPLC (HPLC area %) | Total impurities ≤2.5% @220 nm Target - No individual impurity >1.0% |
| Water Content USP <921> | Report |
| Residual Solvents | Per ICH guidelines (report individual and total solvents) |
| Residue on Ignition (ROI) USP <281> | Report (Target NMT 0.1%) |
| $^1$H-NMR USP <761> | Consistent with structure |
| Melting Point (DSC) | Report |
| TGA | Report |
| LC-MS | Report mass ion |

HPLC Method (for Details, see Appendix A):

For the HPLC, Comparison of impurity profiles at 220 nm is expected. A solution stability of DEGD (90I) in the HPLC sample diluents shall be run as follows:

| Solution Stability | Main Band: 97.0-103.0% of initial No new/changing peaks >0.5% of nominal main band concentration | Storage requirements and stability time should be sufficient for the intended use of the method (e.g. 2-7 days at ambient conditions) |
|---|---|---|

Reporting Practices Impurities by HPLC:

Integrate all peaks greater than and/or equal to 0.05% except those due to the diluent/blank, and tabulate area percent each peak by relative retention times (RRT).

Area percent impurity A=peak area impurity A×100. Total peak area of main component and impurities.

Forced Degradation Study

A forced degradation study should be executed on the DEGD, with the results analyzed by observation of visual changes and by HPLC (and LC-MS if unknown peaks are seen greater than 0.05%) and data included in the GLP report. The following should be executed for 24 h at 50° C. or up to 5 days if no impurities are seen at 24 and 72 h: DEGD Control, 0.1N HCl, 0.1N NaOH, 0.1% $H_2O_2$.

Final Report on GLP Synthesis

The following is a brief description of the process used to manufacture/isolate the GLP DEGD (90I) including the following details:

Discuss the synthetic route used to manufacture the material, detailing steps taken to purify the final DEGD or starting materials. Provide the flow diagram of the synthetic route supplemented by any other specific testing that was used, especially if non-standard procedures were used (e.g., special purification) and any additional tests that give assurance of purity (e.g., TLC, etc.). Provide an overview table of all raw materials/solvents used in the synthesis (with grade and or specification, as appropriate). Include in the synthesis description the charge quantity (mass and molar) of all materials by step. Include storage conditions (if not taken directly to the next step) and quantities of isolated intermediates and measured quantities (grams or mL) of side streams. Address the steps and tests performed to assure purity profile and related non-HPLC assay tests (i.e. water content, ROI, GC-residual solvents) Include Mass Spectrometry, NMR and HPLC data needed to assign structural ID and purity of the final isolated DEGD. This analytical information will be provided in the form of a Certificate of Analysis as per Section 2 and this CofA will be included as an addendum to the Report. Include copies of relevant chromatograms and spectra. All must be clean, legible, and appropriately labeled. (See detailed instructions below).

Mass Spectrometry on DEGD (90I)

The following data are included: (1) Brief details on how the spectrum was obtained. (2) Data which establishes the molecular weight. Preferably this will be the electron impact spectrum. If not, show data from another ionization technique. (3) Clearly annotated copies of any spectra.

Nuclear Magnetic Resonance Spectroscopy on DEGD (90I)

Include the following data: (1) The $^1$H and $^{13}$0 spectra. (2) Brief details on how spectra obtained. (3) A table showing chemical shift and their assignments. A table showing the multiplicities and number of protons for the proton spectra. (4) Suitably labeled/annotated (e.g., protons as a, b, c, etc.) molecular structures. (5) Include data from further NMR experiments if they are necessary to clarify assignments or to remove structural ambiguities. Provide discussion of how these experiments were used to assign the proton and carbon spectra. Include copies of the spectra.c Infrared Spectroscopy on DEGD (90I)

Include the following data: (1) Brief details on how the spectrum was obtained. (2) A table showing the assignment of absorption against functional group. Include appropriate footnotes that explain the interpretation of this table. (3) A clearly annotated copy of the spectrum.

Section 4: GMP Synthesis

The goal of this section is to produce at least 20 kgs of DEGD, preferably as a single lot if possible, by the synthetic scheme(s) in Section 1 or following an improved process developed as a result of the work described in Section 1.

As discussed above, for the synthesis of DEGD (90I), J-star will source the diethylene glycol and/or benzoic acid as starting materials. The starting materials should be of high purity, with low levels of known contaminants: Diethylene glycol: low ethylene glycol content; Benzoic acid: low benzaldehyde and benzyl alcohol content.

The DEGD (90I) should be tested to confirm absence of diethylene glycol to meet USP standards similar to the diethylene glycol level in glycerol.

Deliverables:

~20 kgs of GMP DEGD; Executed batch records; CofA with analytical package (raw data); CofC; and Analytical data (including CofAs) on starting materials; DEGD on stability.

The following tests will be executed on the GMP synthesis materials and create a CofA:

TABLE 6

| TEST NAME | ACCEPTANCE LIMITS |
|---|---|
| Appearance (visual inspection) | Report |
| FT-IR USP <197> | Consistent with structure |
| HPLC (HPLC area %) | Retention time of main peak consistent with reference standard |
| Impurities by HPLC (HPLC area %) | Total impurities ≤2% @220 nm Target - No individual impurity >0.5% Diethylene glycol impurity ≤0.05% |
| Water Content USP <921> | Report |
| Residual Solvents | Per ICH guidelines (report individual and total solvents) |
| Residue on Ignition (ROI) USP <281> | Report (Target NMT 0.1%) |
| Assay by HPLC | 97.0% to 103.0% (report as anhydrous, solvent free basis) |
| $^1$H-NMR USP <761> | Consistent with structure |
| Elemental Impurities USP <232> | Conforms for oral drug (Class 1 and 2A) |
| Melting Point (DSC) | Report |
| TGA | Report |
| LC-MS | Report mass ion |

Stage 4 (Cont.): GMP Lot Stability

The GMP API (i.e. active pharmaceutical ingredient) batch should be placed on stability. The DEGD for the stability study should be packaged in the same materials of construction container that the GMP batch was packaged.

The request is for a two year stability study under the following conditions.

TABLE 7

| | Time Points | | | | | | |
|---|---|---|---|---|---|---|---|
| Condition | Initial | 1 month | 3 months | 6 months | 9 months | 12 months | 18 months | 24 months |
| 25° C./60% RH | X | X | X | X | X | X | X | X |
| 40° C./75% RH | | X | X | X | OP | OP | OP | OP |

Referring to Table 7, X=Testing (appearance, assay, related substances and water content) to be conducted at this time point, and OP=Optional testing (results dependent and not planned as part of this study).

APPENDIX A: ANALYTICAL DATA

API Physical State:

Clear colorless liquid but solidified to an opaque white crystalline solid. DEGD becomes liquid at temperatures in the range 24-33° C. and has a very low volatility (Vp=0.000017 Pa at 25° C./0.096 mm Hg) and is water miscible. DEGD is moderately lipophilic (i.e. tending to combine with or dissolve in lipids or fats) with a log $K_{OW}$ of 3.0-3.2.

API Physical Properties:

BP: 225-227° C.@ 3 mm

Decomposition: >230° C.

Water solubility: 0.193 g/L

Log P: 3.04

Flash Point: 232° C.

Viscosity: 110 mPa·S

Density: 1.2 @ 20° C.

Impurities Expected to be Present in API:

Dipropylene glycol dibenzoate; Ethylene glycol dibenzoate; Propylene glycol dibenzoate; n-Propyl benzoate; and Diethylene glycol monobenzoate.

HPLC Method (Lab):

HPLC Method Conditions

TABLE 8

| System | HP Agilent 1100 | | | |
|---|---|---|---|---|
| Column | Gemini C18 5 um 110A 150*4.6 mm | | | |
| Mobile phase A | 0.1% TFA in $H_2O$ | | | |
| Mobile phase B | 0.075% TFA in ACN | | | |
| Gradient | Time (min) | Flow rate (mL/min) | % MPA | % MPB |
| | 0 | 1.0 | 70 | 30 |
| | 5 | 1.0 | 70 | 30 |
| | 25 | 1.0 | 40 | 60 |
| | 25.5 | 1.0 | 0 | 100 |
| | 30.5 | 1.0 | 0 | 100 |
| | 31 | 1.0 | 70 | 30 |
| | 36 | 1.0 | 70 | 30 |
| Run Time | 36 min | | | |
| Autosampler Temperature | 2-8° C. | | | |
| Column Temperature | 50° C. | | | |
| Detection | UV 220 nm | | | |
| Injection volume | 5 μL | | | |
| Diluent | 50:50 ACN:$H_2O$ | | | |

HPLC Solution Preparation

Diluent: Mix 50 mL ACN and 50 mL $H_2O$ well and sonicate to remove bubbles.

Standard Solution 1: Obtained from AccuStandard®, concentration is 1012 μg/mL and Lot # is 220061203.

Standard Solution 2: Weigh out 41.02 mg Di(ethylene glycol) dibenzoate (Sigma-Aldrich, Lot #MKCC0532) into a 25-mL volumetric flask, add diluent to dissolve it and up to the volume.

Sample Solution: Weigh out 30.75 mg Di(ethylene glycol) dibenzoate into a 25-mL volumetric flask, add diluent to dissolve it and up to the volume.

1.1 Specificity (1) Inject Blank (diluent), standard and sample into HPLC. (2) Acceptance criteria: The analyte should have no interference from other extraneous components and be well resolved from them.

Figure 22:
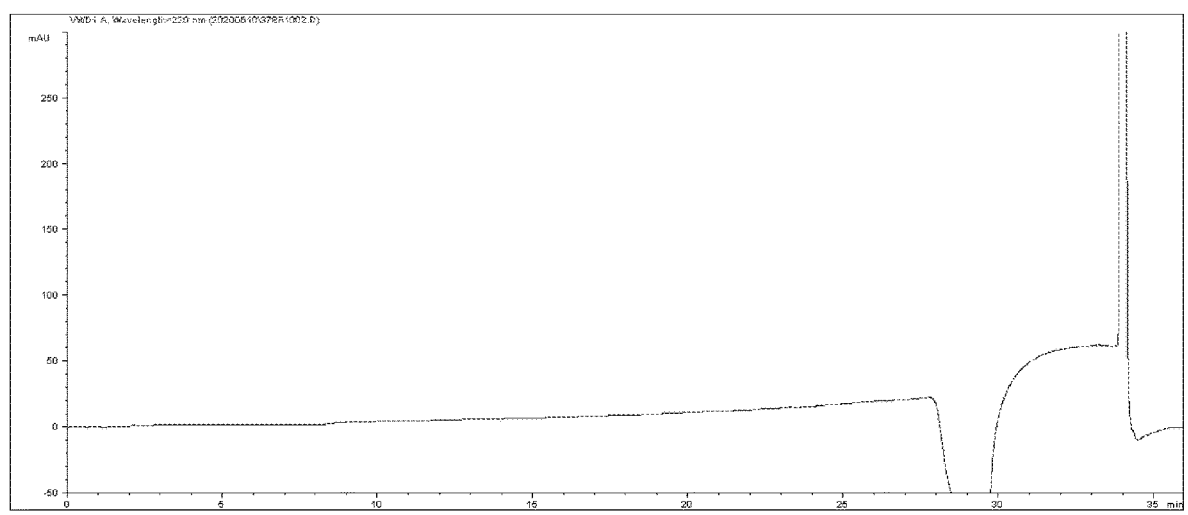
FIG. 22 illustrates a graph of a representative chromatogram of diluent.

FIG. 22 illustrates a graph of a representative chromatogram of diluent.

Figure 23:
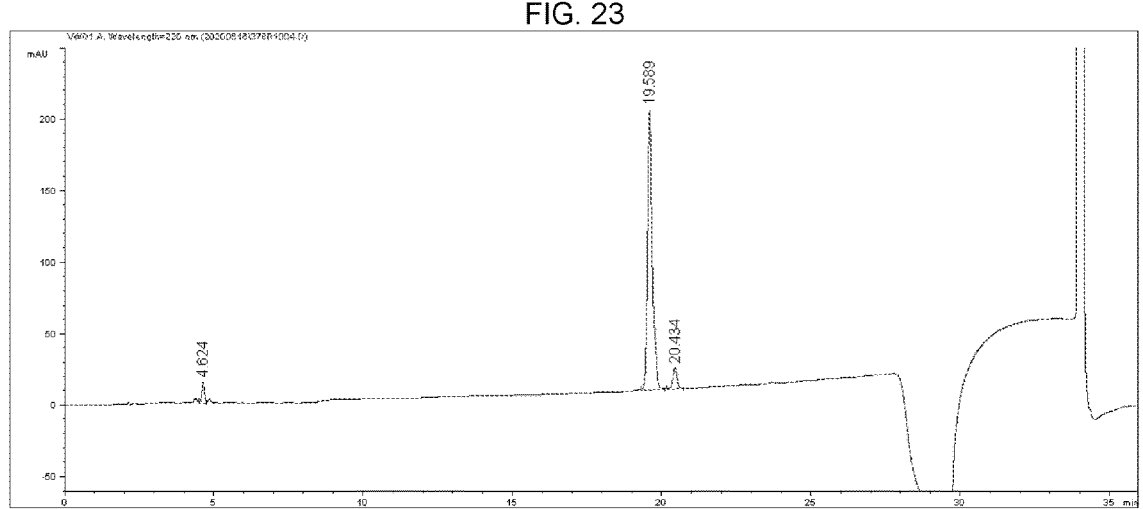
FIG. 23 illustrates a graph of a representative chromatogram of standard.

FIG. 23 illustrates a graph of a representative chromatogram of standard.

Figure 24:
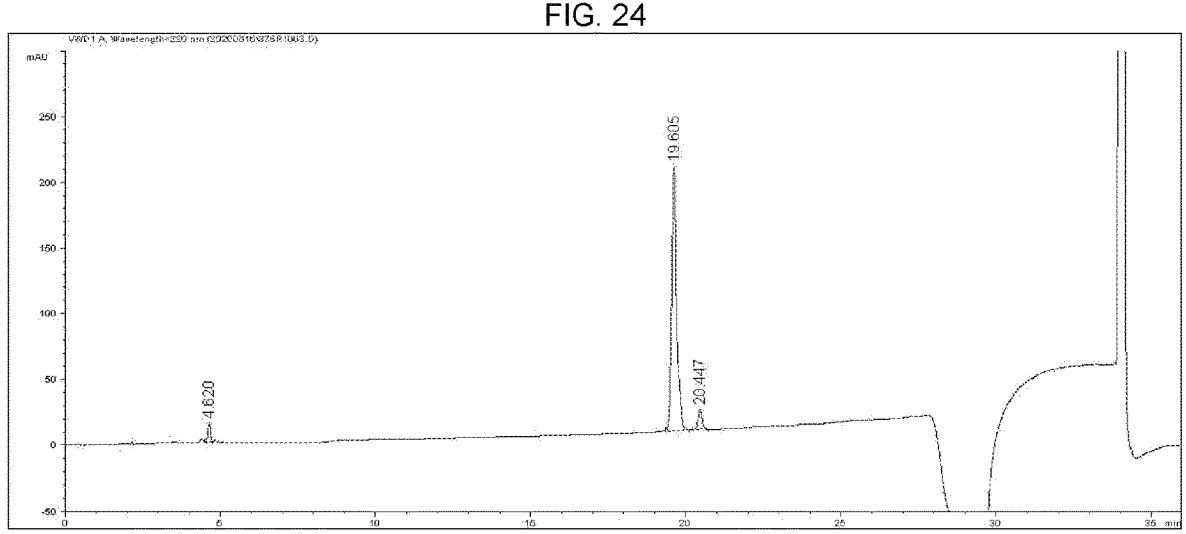
FIG. 24 illustrates a graph of a representative chromatogram of sample.

FIG. 24 illustrates a graph of a representative chromatogram of sample.

Figure 25A:
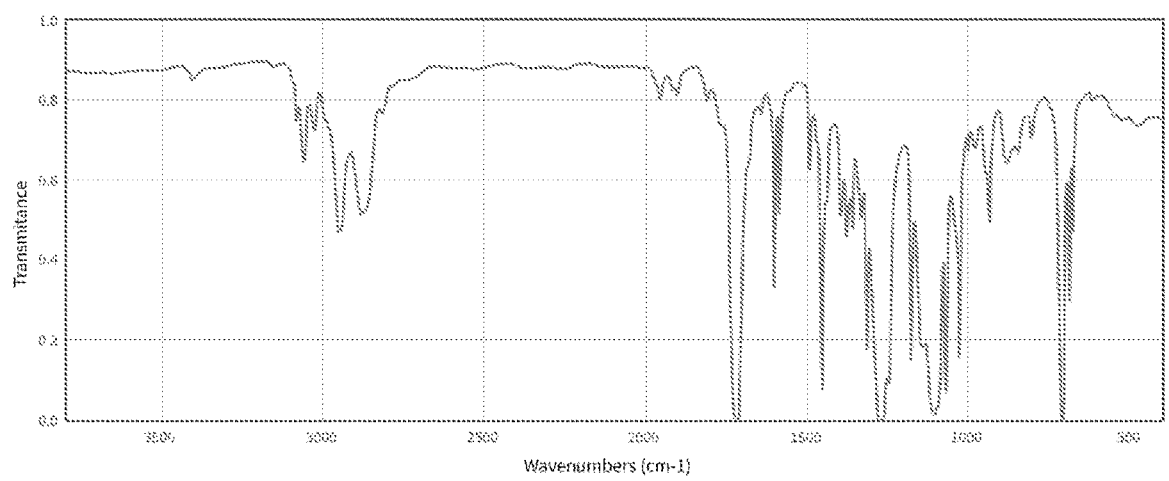
FIG. 25A illustrates an infrared spectrum image of 90I, according to an exemplary embodiment of the present general inventive concept.

FIG. 25A illustrates an infrared spectrum image of 90I, according to an exemplary embodiment of the present general inventive concept.

See https://webbook.nist.gov/cgi/cbook.cgi?ID=C120558&Type=IR-SPEC&Index=0#IR-SPEC.

Figure 25B:
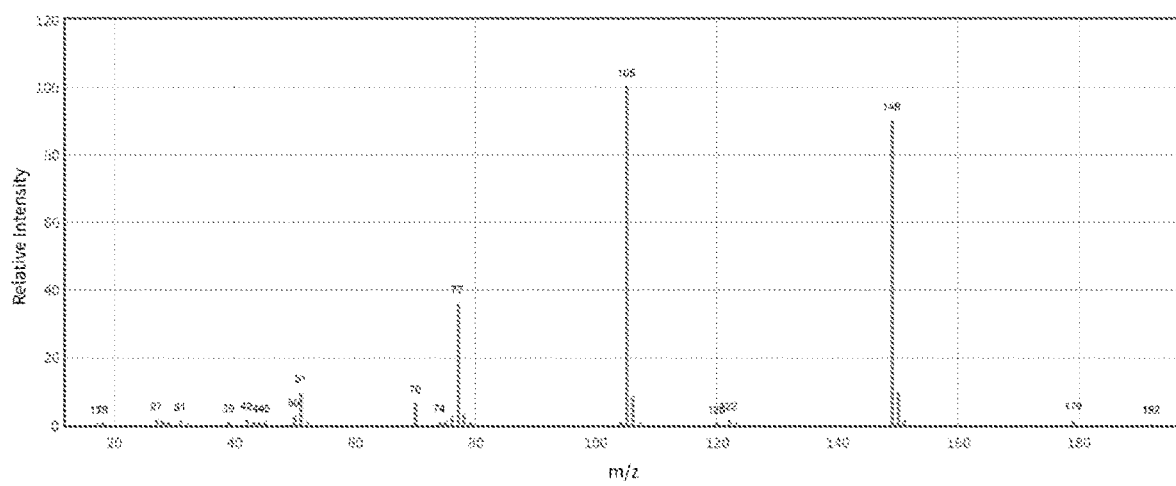
FIG. 25B illustrates a mass spectrum image of 90I, according to an exemplary embodiment of the present general inventive concept.

FIG. 25B illustrates a mass spectrum image of 90I, according to an exemplary embodiment of the present general inventive concept.

See https://webbook.nist.gov/cgi/cbook.cgi?ID=C120558&Mask=200#Mass-Spec.

A Molbase render of 90I (DEGD). See http://www.molbase.com/en/hnmr_120-55-8-moldata-25011.html.

APPENDIX B: DEGD TOXICOLOGY DATA

Metabolism of DEGD was studied in Sprague-Dawley CD rats after single oral doses of 50 mg/kg (low level) and 750 mg/kg (high level). Almost all of single oral doses of 50 and 750 mg/kg of DEGD administered to the rats were adsorbed, metabolized and excreted in the urine within 24 hours of administration. DEGD was metabolized via hydrolysis of the ester bonds to benzoic acid. The free acid was then conjugated with either glycine (major pathway) or glucuronic acid (minor pathway) prior to excretion.

DEGD has low acute toxicity by the oral route in rats with $LD_{50}$ reported at 4,198 mg/kg bw (OECD 401). Dermal $LD_{50}$ in rats was found to be greater than 2,000 mg/kg bw (OECD 402). An acute inhalation toxicity study in the rat was conducted with DEGD resulting in an $LC_{50}$ greater than 200 mg/L (4 h).

No dermal reaction was reported following a single semi-occlusive application of DEGD to intact rabbit skin for four hours. A single instillation of DEGD into the eye of the rabbit elicited transient very slight conjunctival irritation only. No allergic skin reaction was reported in guinea pigs after repeated skin contact (intradermal and topical) using the Magnusson and Kligman method.

Subchronic toxicity was studied in a repeated dose thirteen week oral toxicity study in the rat (OECD 408). Animals received DEGD in the diet in concentration levels of 250, 1000, 1750 or 2500 mg/kg/day. A NOAEL of 1,000 mg/kg bw was established based on the results of the study. There were no findings of toxicological importance at a dosage of 1,000 mg/kg/day or below. In animals receiving 1,750 or 2,500 mg/kg/day, there was an adverse effect on bodyweight gain, changes in clinical pathology parameters and an increased incidence/degree of haemosiderosis (i.e. an overload of iron in organs and/or tissues) in the spleen. In addition, at 2,500 mg/kg/day, a few treatment-related clinical signs were evident, minimal periportal hepatocyte hypertrophy was noted in both sexes. When selected animals previously receiving 2,500 mg/kg/day were maintained off-dose for 4-weeks, all treatment related changes showed evidence of recovery or recovered completely.

No effects were reported in dogs administered up to 300 mg/kg/day of DEGD in their diet for 90 days.

DEGD did not demonstrate mutagenic potential in bacterial (Ames test, OECD 471/2) or mammalian cell (mouse lymphoma cells, OECD 476) systems with and without metabolic activation. No response considered to be indicative of clastogenic (i.e. a mutagenic agent giving rise to or inducing disruption or breakages of chromosomes, leading to sections of the chromosomes being deleted, added, or rearranged) activity was observed in a In-vitro Mammalian Chromosome Aberration Test in CHL cells (OECD 473).

Prenatal developmental toxicity of DEGD (purity 97.67%) in rats was studied in a test according to US EPA 870.3700 Harmonized Guideline (corresponding to OECD 414). Animals were administered doses of 250, 500 and 1,000 mg/kg/day in the diet. NOEL for maternal toxicity was found to be 1,000 mg/kg/day. At 1,000 mg/kg/day, there were no detectable signs of maternal toxicity; there were no maternal deaths and all females had a live litter at sacrifice. NOAEL for prenatal development was found to be 500 mg/kg/day. A small number of fetuses with cervical ribs was seen at 1,000 mg/kg/day, but not considered indicative of substantial disturbance of morphological development. NOEL for fetal growth and development was 250 mg/kg/day. At 1,000 mg/kg/day mean fetal weights, and consequently litter weight were slightly lower than the control, combined with fetal weight and female fetal weight attaining statistical significance. At 1,000 mg/kg/day 4 fetuses showed cervical ribs, this incidence being higher than the concurrent control and marginally outside the current background control data. Although the incidence of this finding was relatively low, it is considered that a treatment relationship could not be ruled out.

Reproductive toxicity of DEGD (purity 97.67%) in rats was studied in a 2-generation test according to OECD 416 and at dose levels of 1000, 3300 or 10000 ppm in the diet corresponding to 50, 165 and 500 mg/kg bw/day based on standard conversion factors. There were no obvious toxicological effects of treatment for the two generations on the general condition of the parental animals although a slight disturbance in the pattern of maternal weight change was noted at 10,000 ppm in both generations and at 3,300 ppm in the $F_I$ generation. There was no effect on fertility and reproductive performance at any of the dietary inclusion levels in either generation. Litter parameters at birth of the $F_I$ and $F_2$ progeny and their survival to weaning showed no apparent detrimental effects of treatment. However, for the F2 offspring at 10,000 ppm there was a reduction in weight gain from birth to weaning. No abnormal findings were apparent at necropsy of the $F_O$ or $F_I$ parental animals, the post weaned unselected $F_I$ offspring or the $F_2$ offspring. Organ weight assessment of the $F_O$ and $F_I$ parent animals did not suggest any adverse effects on any organs. Assessment of spermatogenesis and histopathology in both parental generations showed that there were no injurious effects on the testes or other reproductive organs.

Furthermore, detailed histopathological examination of the tissues from both sexes in both generations did not reveal any adverse effects of treatment. The only possible effect of treatment detected at assessment of organ weights from FI and F2 offspring was lower absolute and bodyweight relative spleen weights among F2 males and females compared with controls. The evidence from this study suggested that a dietary concentration of 10,000 ppm (500 mg/kg bw/day) should be considered as the NOAEL for the $F_O$ and $F_I$ parent animals. The NOAEL for the developing offspring is considered to be 3,300 ppm (165 mg/kg bw/day). The NOEL for reproductive parameters is considered to be 10,000 ppm (500 mg/kg bw/day).

Evaluation of estrogenic activity at doses of 500, 1000, 1500 or 2000 mg/kg/day for 7 days by oral gavage in ovariectomized adult Spraque-Dawley (CD) rats using vaginal cornification and the uterotrophic response as the endpoints demonstrated that DEGD did not exhibit estrogenic activity up to and including the maximally tolerated dose.

In summary the following profile was identified:

TABLE 9

| Acute toxicity | | | | | |
|---|---|---|---|---|---|
| $LD_{50}$, | $LD_{50}$, | $LC_{50}$, | Local effects and sensitisation | | |
| oral mg/kg bw | dermal mg/kg bw | inhal.. mg/m$^3$ | Skin irritation | Eye irritation | Sensitisation |
| 4,198 | >2,000 | >200 mg/L | No irritation | Slight irritation | Not sensitising |

TABLE 10

| Repeat dose, genotoxicity, carcinogenicity | | | Maternal | Reproductive toxicity | | |
|---|---|---|---|---|---|---|
| Repeat dose, NOAEL mg/kg bw/day | Genotoxicity | Carcinogenicity | toxicity mg/kg bw/day | NOAEL mg/kg bw/day | Reproductive toxicity | Critical endpoint |
| 1,000 | Negative | ND | 1,000 | 500 250 (NOEL) | R: No D: Yes | Fetal bw Cervical ribs |

Environmental Assessment

DEGD (90I) is found to be readily biodegradable (93% of ThOD in 28 days) in the modified Sturm test (OECD 301B) while in the Closed Bottle Test (OECD 301D) the BOD5/COD ratio was only 0.32 (greater than 0.5 required for ready biodegradability). A $K_{OC}$ of 540 indicates rather low mobility of DEGD in soil, and a moderately high calculated BCF of 120 indicates some bioaccumulation potential.

The aquatic toxicity of DEGD is quite uniform in short term/acute OECD tests between the three main standard groups of test organisms; fish, crustaceans and algae. Thus, the acute (96 h) LC50 to fish (*Pimephales promelas*) is 3.9 mg/L, while the EC50 (48 h) for *Daphnia* is 6.7 mg/L and the 72 hours growth rate-based EC50 for algae (*Seleneastrum capricornutum*, now known as *Pseudokirchneriella subcapitata*) is 11 mg/L. This could indicate a non-specific mode-of-action of DEGD.

The acute toxicity to earthworm (*Eisenia foetida*) (14 days) was found to be greater than 1,000 ppm while the inhibitory effect (1050) on the bacterium *Pseudomonas putida* could not be determined specifically but only be stated as higher than the highest testable concentration of 10 mg/L. Activated sludge respiration was not inhibited at 100 mg/L.

TABLE 11

| Environmental fate | | Ecotoxicity | | | | |
|---|---|---|---|---|---|---|
| | | | | | Micro- | |
| Bioaccumulation | Mobility | Fish | Daphnia | Algae | organisms | Terrestrial |
| BCF = 120 (calculated) | $K_{OC}$ = 540 (calculated) | $LC_{50}$ (96 h) = 3.9 mg/L | $EC_{50}$ (48 h) = 6.7 mg/L | $EC_{50}$ (72 h) = 11 mg/L | $EC_{50}$ >10 mg/L (*P. putida*) NOEC ≥100 mg/L, activated sludge | $LC_{50}$ (14 d) >1,000 mg/kg (earthworm) |

Referring to Table 10, included is a summary of environmental fate and ecotoxicity data on DEGD.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. A method for the treatment of a coronavirus disease, comprising:
    administering to a subject in need thereof of an anti-pathogenic compound, such that the anti-pathogenic compound is diethylene glycol dibenzoate, wherein the coronavirus disease is SARS-CoV-2.

2. The method of claim 1, wherein the diethylene glycol dibenzoate is derived from an herbal extract.

3. The method of claim 1, wherein the diethylene glycol dibenzoate is a glycol derivative.

4. The method of claim 1, wherein the diethylene glycol dibenzoate is synthesized from at least one of diethylene glycol and benzoic acid.

5. The method of claim 1, wherein the anti-pathogenic compound is lipophilic.

6. A method of treating a subject infected with COVID-19 comprising administering to the subject in need thereof of an anti-pathogenic compound, diethylene glycol dibenzoate.

7. The method of claim 6, wherein the diethylene glycol dibenzoate is derived from an herbal extract.

8. The method of claim 6, wherein the diethylene glycol dibenzoate is a glycol derivative.

9. The method of claim 6, wherein the diethylene glycol dibenzoate is synthesized from at least one of diethylene glycol and benzoic acid.

10. The method of claim 6, wherein the anti-pathogenic compound is lipophilic.

11. The method of claim 6, wherein the anti-pathogenic compound boosts an immune system of the subject.

12. The method of claim 11, wherein the anti-pathogenic compound boosts the immune system by revitalizing at least one of a dysfunctional monocyte and a dysfunctional macrophage.

13. The method of claim 11, wherein the anti-pathogenic compound boosts the immune system by stimulating production of gamma interferon.

* * * * *